(12) United States Patent
Bös et al.

(10) Patent No.: US 6,756,380 B1
(45) Date of Patent: Jun. 29, 2004

(54) 5-PHENYL-PYRIMIDINE DERIVATIVES

(75) Inventors: Michael Bös, Montreal (CA); Guido Galley, Rheinfelden (DE); Thierry Godel, Basel (CH); Torsten Hoffmann, Birsfelden (CH); Walter Hunkeler, Magden (CH); Patrick Schnider, Oberwil (CH); Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/575,789

(22) Filed: May 22, 2000

(30) Foreign Application Priority Data

May 31, 1999  (EP) .............................................. 99110482

(51) Int. Cl.[7] ................... C07D 239/32; C07D 239/26; A61K 31/505
(52) U.S. Cl. ..................... 514/274; 514/273; 514/272; 514/269; 514/252.19; 514/252.2; 514/252.18; 514/252.14; 514/235.8; 544/295; 544/122; 544/123; 544/319; 544/335; 544/333; 544/323; 544/324; 544/328; 544/329
(58) Field of Search ............................... 544/295, 122, 544/123, 319, 335, 333, 323, 324, 328, 329; 514/235.8, 252.14, 252.18, 252.2, 252.19, 269, 272, 273, 274

(56) References Cited

U.S. PATENT DOCUMENTS 4,015,000 A    3/1977  Kocsis et al. ........... 260/243 C

FOREIGN PATENT DOCUMENTS

| WO | WO 95/18124 | 7/1995 |
| WO | WO 97/09315 | 3/1997 |

OTHER PUBLICATIONS

Neurosci. Res., 1996, 7, 187–214, Roger Barker.
Can. J. Phys., 1997, 75, 612–621, Longmore et al.
Science, 1998, 281, 1640–1645, Kramer et al.
Tachykinin Receptor and Tachykinin Receptor Antagonists, J. Auton. Pharmacol., 13, 23–93, 1993, Naggi et al.
The New England Journal of Medicine, vol. 340, No. 3 190–195, 1999, Navari et al.

*Primary Examiner*—John M. Ford
(74) *Attorney, Agent, or Firm*—George W. Johnston; Patricia S. Rocha-Tramaloni; Eileen M. Ebel

(57) ABSTRACT

Compounds of the general formula are described:

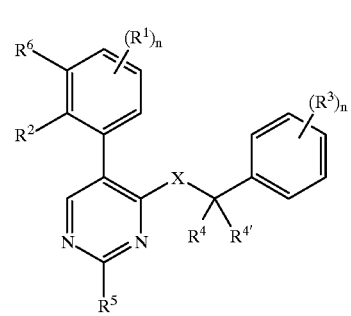

wherein
$R^1$ is hydrogen or halogen;
$R^2$ is hydrogen, halogen, lower alkyl or lower alkoxy;
$R^3$ is halogen, trifluoromethyl, lower alkoxy or lower alkyl;
$R^4/R^{4'}$ are each independently hydrogen or lower alkyl;
$R^5$ is lower alkyl, lower alkoxy, amino, hydroxy, hydroxy-lower alkyl, —$(CH_2)_n$-piperazinyl, optionally substituted by lower alkyl, —$(CH_2)_n$-morpholinyl, —$(CH_2)_{n+1}$-imidazolyl, —O—$(CH_2)_{n+1}$-morpholinyl, —O—$(CH_2)_{n+1}$-piperidinyl, lower alkyl-sulfanyl, lower alkyl-sulfonyl, benzylamino, —NH—$(CH_2)_{n+1}$N$(R^{4''})_2$, —$(CH_2)_n$—NH—$(CH_2)_{n+1}$N$(R^{4''})_2$, —$(CH_2)_{n+1}$N$(R^{4''})_2$, or —O—$(CH_2)_{n+1}$N$(R^{4''})_2$, wherein $R^{4''}$ is hydrogen or lower alkyl;
$R^6$ is hydrogen;
$R^2$ and $R^6$ or $R^1$ and $R^6$ may together be —CH=CH—CH=CH—, wherein $R^2$ and $R^6$ or $R^1$ and $R^6$, respectively, together with the two carbon ring atoms to which they are attached form a fused ring, with the proviso that n for $R^1$ is 1;
n is independently 0–2; and
X is —C(O)N($R^{4''}$)— or —N($R^{4''}$)C(O)—;
and pharmaceutically acceptable acid addition salts thereof.

15 Claims, No Drawings

5-PHENYL-PYRIMIDINE DERIVATIVES

BACKGROUND OF THE INVENTION

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The neuropeptide receptors for substance P (NK-1) are widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, is reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol.340, No. 3 190–195, 1999 has been described the reduction of cisplatin-induced emesis by a selective neurokinin-1-receptor antagonist.

SUMMARY OF THE INVENTION

The present invention relates to compounds of the general formula

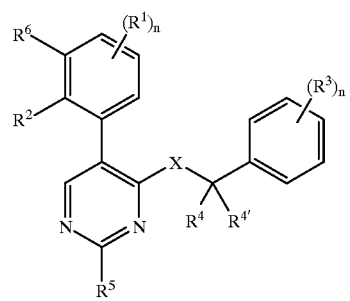

I wherein $R^1$ is hydrogen or halogen;

$R^2$ is hydrogen, halogen, lower alkyl or lower alkoxy;

$R^3$ is halogen, trifluoromethyl, lower alkoxy or lower alkyl;

$R^4$ and $R^{4'}$ are each independently other hydrogen or lower alkyl;

$R^5$ is lower alkyl, lower alkoxy, amino, hydroxy, hydroxy-lower alkyl, —$(CH_2)_n$-piperazinyl optionally substituted by lower alkyl, —$(CH_2)_n$-morpholinyl, —$(CH_2)_{n+1}$-imidazolyl, —O—$(CH_2)_{n+1}$-morpholinyl, —O—$(CH_2)_{n+1}$-piperidinyl, lower alkyl-sulfanyl, lower alkyl-sulfonyl, benzylamino, —NH—$(CH_2)_{n+1}N(R^{4''})_2$, —$(CH_2)_n$—NH—$(CH_2)_{n+1}N(R^{4''})_2$, —$(CH_2)_{n+1}N(R^{4''})_2$, or —O—$(CH_2)_{n+1}N(R^{4''})_2$, wherein $R^{4''}$ is hydrogen or lower alkyl;

$R^6$ is hydrogen;

$R^2$ and $R^6$ or $R^1$ and $R^6$ may together be —CH=CH—CH=CH—, wherein $R^2$ and $R^6$ or $R^1$ and $R^6$, respectively, together with the two carbon ring atoms to which they are attached form a fused ring, with the proviso that n for $R^1$ is 1;

n is independently 0–2; and

X is —C(O)N($R^{4''}$)— or —N(O)—;

and to pharmaceutically acceptable acid addition salts thereof.

The compounds of formula I and their salts are characterized by valuable therapeutic properties. It has been surprisingly found that the compounds of the present invention are antagonists of the Neurokinin 1 (NK-1, substance P) receptor.

DETAILED DESCRIPTION OF THE INVENTION

The present invention relates to compounds of the general formula

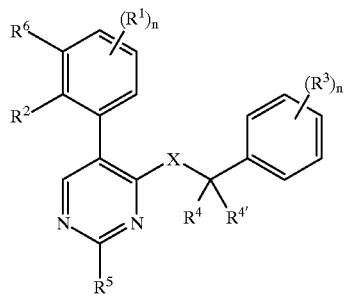

I wherein
- R¹ is hydrogen or halogen;
- R² is hydrogen, halogen, lower alkyl or lower alkoxy;
- R³ is halogen, trifluoromethyl, lower alkoxy or lower alkyl;
- R⁴ and R⁴' are each independently other hydrogen or lower alkyl;
- R⁵ is lower alkyl, lower alkoxy, amino, hydroxy, hydroxy-lower alkyl, —(CH$_2$)$_n$-piperazinyl optionally substituted by lower alkyl, —(CH$_2$)$_n$-morpholinyl, —(CH$_2$)$_{n+1}$-imidazolyl, —O—(CH$_2$)$_{n+1}$-morpholinyl, —O—(CH$_2$)$_{n+1}$-piperidinyl, lower alkyl-sulfanyl, lower alkyl-sulfonyl, benzylamino, —NH—(CH$_2$)$_{n+1}$N(R⁴")$_2$, —(CH$_2$)$_n$—NH—(CH$_2$)$_{n+1}$N(R⁴")$_2$, —(CH$_2$)$_{n+1}$N(R⁴")$_2$, or —O—(CH$_2$)$_{n+1}$N(R⁴")$_2$, wherein R⁴" is hydrogen or lower alkyl;
- R⁶ is hydrogen;
- R² and R⁶ or R¹ and R⁶ may together be —CH═CH—CH═CH—, wherein R² and R⁶ or R¹ and R⁶, respectively, together with the two carbon ring atoms to which they are attached form a fused ring, with the proviso that n for R¹ is 1;
- n is independently 0–2; and
- X is —C(O)N(R⁴")— or —N(O)—;

and to pharmaceutically acceptable acid addition salts thereof.

The compounds of formula I and their salts are characterized by valuable therapeutic properties. It has been surprisingly found that the compounds of the present invention are antagonists of the Neurokinin 1 (NK-1, substance P) receptor.

The present invention provides the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

The most preferred indications in accordance with the present invention are those which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

The following definitions of the general terms used in the present description apply irrespective of whether the terms in question appear alone or in combination. As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are groups with 1–4 carbon atoms.

The term "lower alkoxy" denotes a group wherein the alkyl residues are as defined above, and which is attached via an oxygen atom.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Exemplary preferred compounds are those in which X is —C(O)N(R⁴")—, wherein R⁴" is methyl and R⁵ is —(CH$_2$)$_n$-piperazinyl, optionally substituted by methyl, and n is 0 or 1, for example the following compounds:

5-(2-chloro-phenyl)-2-(4-methyl-piperazin-1-yl)-pyrimidine-4-carboxylic acid (3,5-bis-trifluoromethyl-benzyl)-methyl-amide, 5-(4-fluoro-2-methyl-phenyl)-2-(4-methyl-piperazin-1-yl)-pyrimidine-4-carboxylic acid (3,5-bis-trifluoromethyl-benzyl)-methyl-amide or 5-(2-chloro-phenyl)-2-(4-methyl-piperazin-1-ylmethyl)-pyrimidine-4-carboxylic acid (3,5-bis-trifluoromethyl-benzyl)-methyl-amide.

Further preferred are compounds in which X is —C(O)N(R⁴")—, wherein R⁴" is methyl nd R⁵ is —O(CH$_2$)$_2$-morpholinyl.

An example of such a compound is 5-(2-chloro-phenyl)-2-(2-morpholin-4-yl-ethoxy)-pyrimidine-4-carboxylic acid (3,5-bis-trifluoromethyl-benzyl)-methyl-amid.

Preferred are further compounds, in which X is —C(O)N(R⁴")—, R⁴" is methyl and R⁵ is —NH(CH$_2$)$_{n+1}$N(CH$_3$)$_2$, —(CH$_2$)$_n$—NH(CH$_2$)$_{n+1}$N(CH$_3$)$_2$ or —O(CH$_2$)$_{n+1}$N(CH$_3$)$_2$, wherein n is 1 or 2, for example the following compounds:

5-(2-chloro-phenyl)-2-(2-dimethylamino-ethylamino)-pyrimidine-4-carboxylic acid (3,5-bis-trifluoromethyl-benzyl)-methyl-amide, 2-(2-dimethylamino-ethylamino)-5-o-tolyl-pyrimidine-4-carboxylic acid (3,5-bis-trifluoromethyl-benzyl)-methyl-amide, 2-(2-dimethylamino-ethylamino)-5-(2-methoxy-phenyl)-pyrimidine-4-carboxylic acid (3,5-bis-trifluoromethyl-benzyl)-methyl-amide, 2-(2-dimethylamino-ethylamino)-5-(4-fluoro-phenyl)-pyrimidine-4-carboxylic acid (3,5-bis-trifluoromethyl-benzyl)-methyl-amide, 2-(2-dimethylamino-ethylamino)-5-(4-fluoro-2-methyl-phenyl)-pyrimidine-4-carboxylic acid (3,5-bis-trifluoromethyl-benzyl)-methyl-amide, 5-(2-chloro-phenyl)-2-(3-dimethylamino-propoxy)-pyrimidine-4-carboxylic acid (3,5-bis-trifluoromethyl-benzyl)-methyl-amide, 5-(2-chloro-phenyl)-2-(2-dimethylamino-ethoxy)-pyrimidine-4-carboxylic acid (3,5-bis-trifluoromethyl-benzyl)-methyl-amide,
2-(2-dimethylamino-ethoxy)-5-o-tolyl-pyrimidine-4-carboxylic acid (3,5-bis-trifluoromethyl-benzyl)-methyl-amide,
2-(3-dimethylamino-propoxy)-5-o-tolyl-pyrimidine-4-carboxylic acid (3,5-bis-trifluoromethyl-benzyl)-methyl-amide,
2-(2-dimethylamino-propoxy)-5-(2-methoxy-phenyl)-pyrimidine-4-carboxylic acid (3,5-bis-trifluoromethyl-benzyl)-methyl-amide,
2-(3-dimethylamino-propoxy)-5-(4-fluoro-2-methyl-phenyl)-pyrimidine-4-carboxylic acid (3,5-bis-trifluoromethyl-benzyl)-methyl-amide,
2-(2-dimethylamino-ethoxy)-5-(4-fluoro-2-methyl-phenyl)-pyrimidine-4-carboxylic acid (3,5-bis-trifluoromethyl-benzyl)-methyl-amide or
5-(2-chloro-phenyl)-2-[(2-dimethylamino-ethylamino)-methyl]-pyrimidine-4-carboxylic acid (3,5-bis-trifluoromethyl-benzyl)-methyl-amide.

Further preferred are compounds, wherein X is —CON($R^{4''}$)$_2$ and $R^{4''}$ is methyl and $R^5$ is $SCH_3$, for example the following compounds:

2-methylsulfanyl-5-o-tolyl-pyrimidine-4-carboxylic acid (3,5-bis-trifluoromethyl-benzyl)-methyl-amide or
5-(4-fluoro-2-methyl-phenyl)-2-methylsulfanyl-pyrimidine-4-carboxylic acid (3,5-bis-trifluoromethyl-benzyl)-methyl-amide.

Other preferred compounds are those, in which X is —CON($R^{4''}$)$_2$ and $R^{4''}$ is methyl and $R^2$ and $R^6$ or $R^1$ and $R^6$ are together —CH=CH—CH=CH—, wherein $R^2$ and $R^6$ or $R^1$ and $R^6$, respectively, together with the two carbon ring atoms to which they are attached form a fused ring, with the proviso that n for $R^1$ is 1, for example the following compounds:

2-(4-methyl-piperazin-1-yl)-5-naphthalen-1-yl-pyrimidine-4-carboxylic acid (3,5-bis-trifluoromethyl-benzyl)-methyl-amide,
2-(2-dimethylamino-ethylamino)-5-naphthalen-1-yl-pyrimidine-4-carboxylic acid (3,5-bis-trifluoromethyl-benzyl)-methyl-amide,
2-(2-dimethylamino-ethoxy)-5-naphthalen-1-yl-pyrimidine-4-carboxylic acid (3,5-bis-trifluoromethyl-benzyl)-methyl-amide,
2-(2-morpholin-4-yl-ethoxy)-5-naphthalen-1-yl-pyrimidine-4-carboxylic acid (3,5-bis-trifluoromethyl-benzyl)-methyl-amide or
2-(3-dimethylamino-propoxy)-5-naphthalen-1-yl-pyrimidine-4-carboxylic acid (3,5-bis-trifluoromethyl-benzyl)-methyl-amide.

Further preferred are compounds, wherein X is —N($R^{4''}$)C(O)—, $R^{4''}$ is lower alkyl and $R^5$ is —$(CH_2)_n$-piperazinyl optionally substituted by lower alkyl, —$(CH_2)_n$-morpholinyl, —NH—$(CH_2)_{n+1}$N$(CH_3)_2$ or —O—$(CH_2)_{n+1}$N$(CH_3)_2$, for example the following compounds:

2-(3,5-bis-trifluoromethyl-phenyl)-N-methyl-N-[2-(4-methyl-piperazin-1-yl)-5-o-tolyl-pyrimidin-4-yl]-isobutyramide,
2-(3,5-bis-trifluoromethyl-phenyl)-N-methyl-N-(2-piperazin-1-yl-5-o-tolyl-pyrimidin-4-yl)-isobutyramide,
2-(3,5-bis-trifluoromethyl-phenyl)-N-methyl-N-(2-morpholin-4-yl-5-o-tolyl-pyrimidin-4-yl)-isobutyramide,
2-(3,5-bis-trifluoromethyl-phenyl)-N-[2-(2-dimethylamino-ethylamino)-5-o-tolyl-pyrimidin-4-yl]-N-methyl-isobutyramide,
2-(3,5-bis-trifluoromethyl-phenyl)-N-[2-(2-dimethylamino-ethoxy)-5-o-tolyl-pyrimidin-4-yl]-N-methyl-isobutyramide,
2-(3,5-bis-trifluoromethyl-phenyl)-N-[5-(2-chloro-phenyl)-2-(4-methyl-piperazin-1-yl)-pyrimidin-4-yl]-N-methyl-isobutyramide or
2-(3,5-bis-trifluoromethyl-phenyl)-N-[5-(2-chloro-phenyl)-2-(2-dimethylamino-ethylamino)-pyrimidin-4-yl]-N-methyl-isobutyramide.

The present compounds of formula I and their pharmaceutically acceptable salts can be prepared by methods known in the art, for example, by processes described below, which process comprises a) reacting a compound of formula

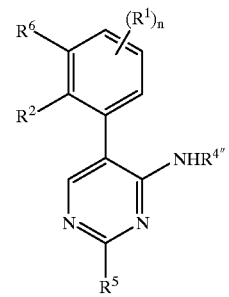

II with a compound of formula

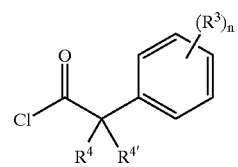

III to a compound of formula

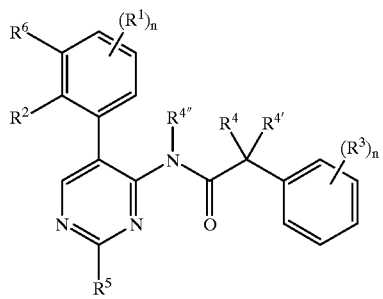

I-1 wherein
R¹–R⁵ and n have the significances given above, or
b) reacting a compound of formula

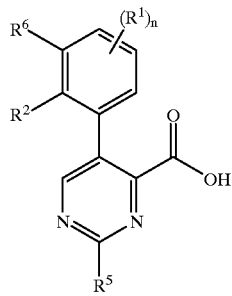

IV with a compound of formula

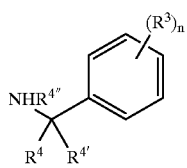

V to give a compound of formula

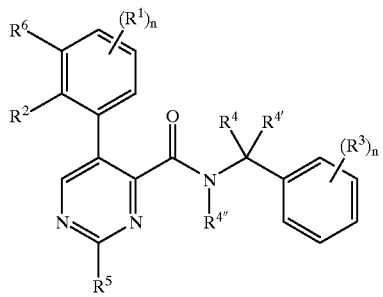

I-2 wherein
R¹–R⁵ and n have the significances given above, and optionally
c) modifying one or more substituents R¹–R⁵ within the definitions given above, and/or if desired, converting the compound obtained into a pharmaceutically acceptable acid addition salt.

In accordance with process variant a), a compound of formula II, for example [5-(2-chloro-phenyl)-2-methylsulfonyl-pyrimidin-4-yl]-methyl-amine is deprotected with KHMDS (potassium hexamethyldisilazide) in THF at 0° for 1 h, and a compound of formula III, for example 2-(3,5-bis-trifluoromethyl-phenyl)-2-methyl-propionyl chloride, is added and the mixture is stirred at room temperature. A typical solvent is N,N-dimethylformamide. The desired compound of formula I-1 is obtained in good yields.

Process variant b) describes the reaction of a compound of formula IV with a compound of formula V to a compound of formula I-2. The reaction is carried out in conventional manner, for example in a solvent, such as dichloromethane in presence of NEt₃, EDCI (N-(3-dimethylaminopropyl)-N'-ethyl-carbodiimide hydrochloride) and HOBT (1-hydroxy-benzotriazole). The mixture is stirred for about 12 hs at room temperature. The desired product is obtained after purification in good yields.

The salt formation is effected at room temperature in accordance with methods which are known per se and which are familiar to any person skilled in the art. Not only salts with inorganic acids, but also salts with organic acids came into consideration. Hydrochlorides, hydrobromides, sulphates, nitrates, citrates, acetates, maleates, succinates, methansulphonates, p-toluenesulphonates and the like are examples of such salts.

The following schemes 1–6 describe the processes for preparation of compounds of formula I in more detail. The starting materials of formulae III, VIII, IX, XII, XIII, XVI, XVII and XXII are known compounds and may be prepared according to methods known in the art.

In the schemes the following abbreviations have been used:

| | |
|---|---|
| THF | tetrahydrofuran |
| DIPEA | N-ethyldiisopropyl-amine |
| HOBT | 1-hydroxy-benzotriazole |
| EDCI | N-(3-dimethylaminopropyl)-N'-ethyl-carbodiimide hydrochloride |
| m-CPBA | m-chloroperbenzoic acid |
| DPPA | diphenylphosphorylazide |
| DMF | dimethylformamide |
| NEt₃ | triethylamine |
| KHMDS | potassium hexamethyldisilazide |

Scheme 1

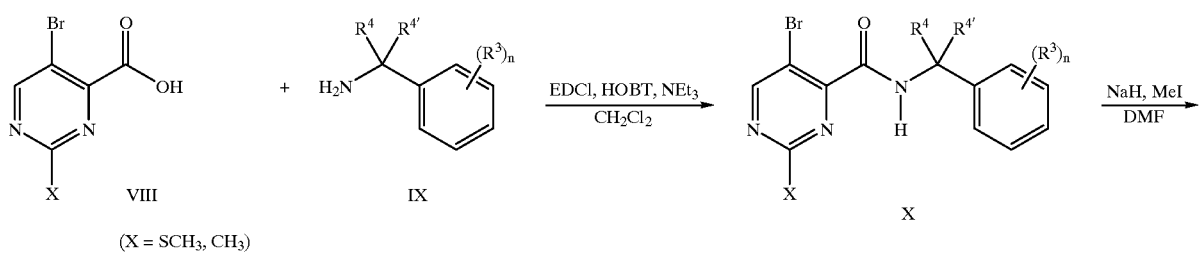

-continued
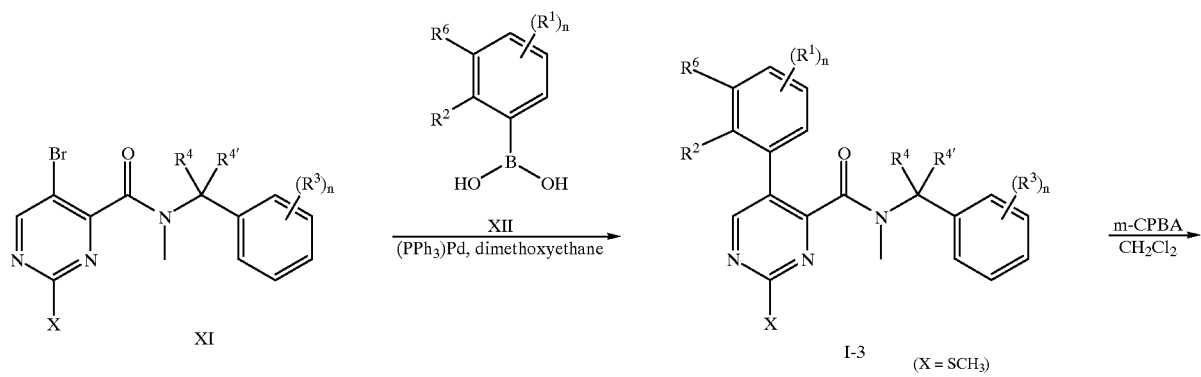
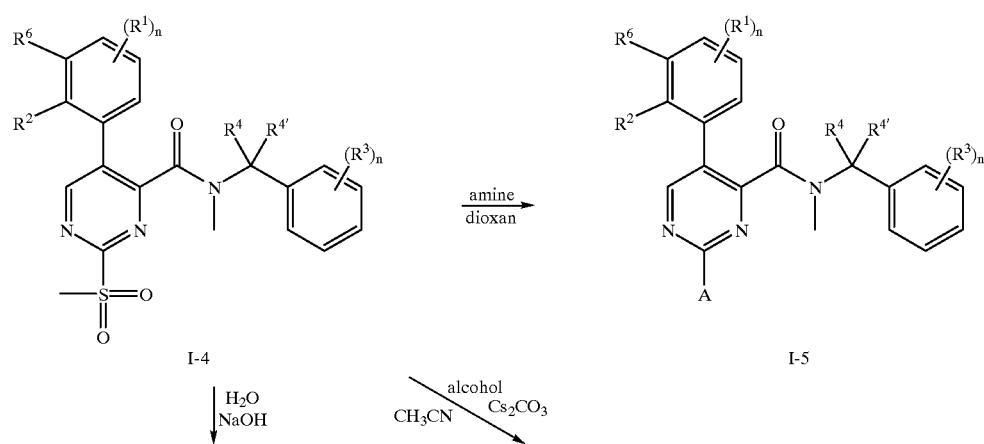
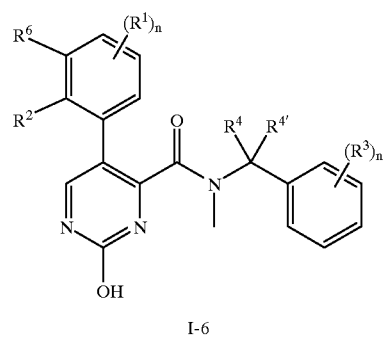
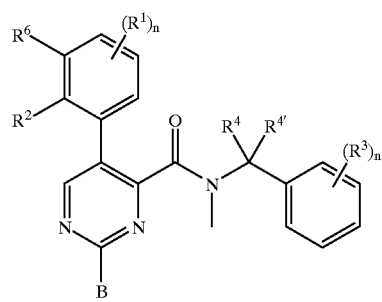

The substituents $R^1$–$R^6$ are given above.
A is an amine group, such as amino or piperazinyl optionally substituted by lower alkyl, morpholinyl, imidazolyl, piperidinyl, benzylamino or —NH—$(CH_2)_{n+1}$N$(R^{4''})_2$, and B is lower alkoxy, —O—$(CH_2)_{n+1}$-morpholinyl, —O—$(CH_2)_{n+1}$-piperidinyl or —O—$(CH_2)_{n+1}$N$(R^{4''})_2$;
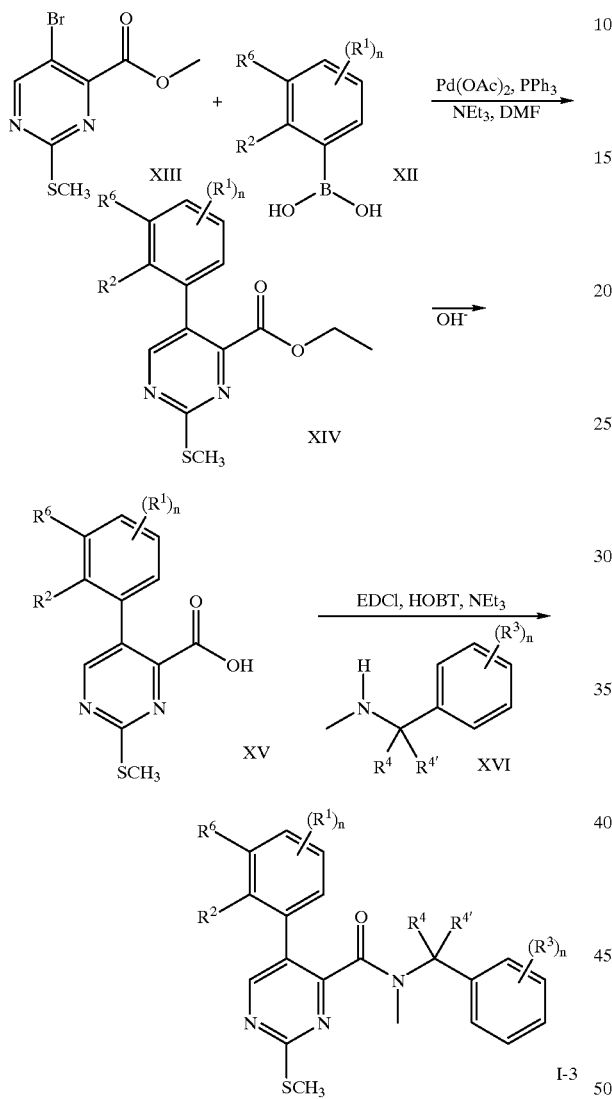
The substituents are given above.
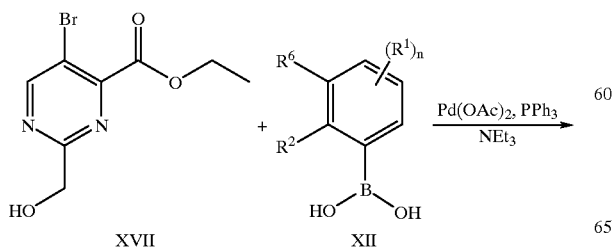
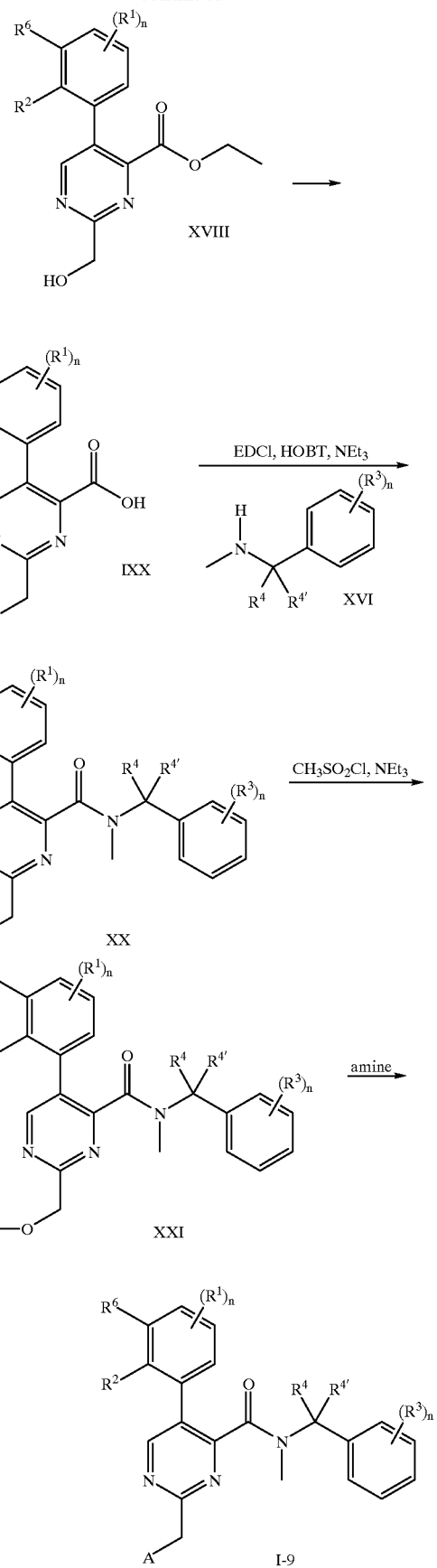

The substituents $R^1$–$R^6$ are given above.
A is an amine group, such as amino or piperazinyl optionally substituted by lower alkyl, morpholinyl, imidazolyl, piperidinyl, benzylamino or —NH—$(CH_2)_{n+1}N(R^{4"})_2$.
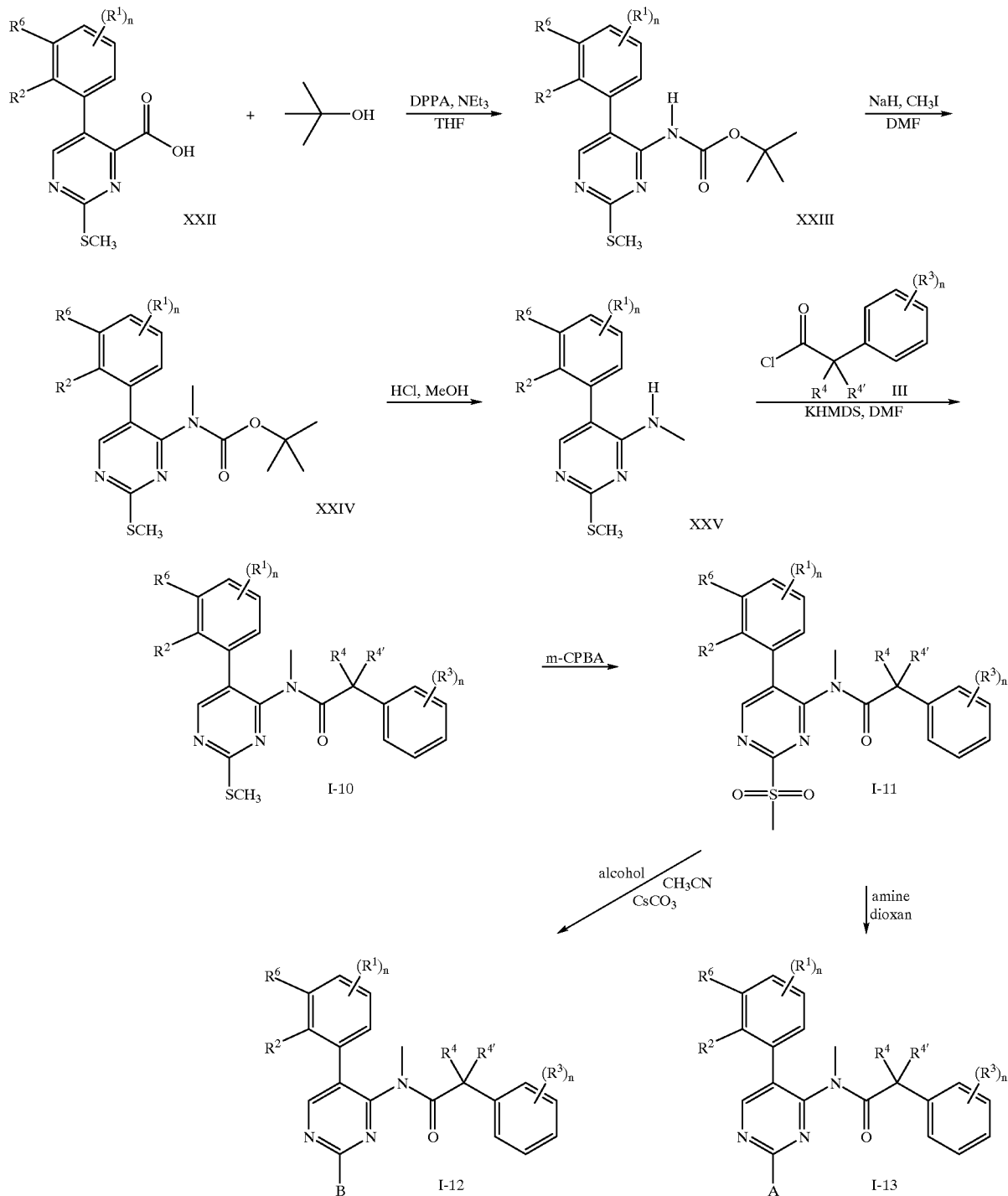
Scheme 4

The substituents R¹–R⁶ are given above.

A is an amine group, such as amino, piperazinyl, optionally substituted by lower alkyl, morpholinyl, imidazolyl, piperidinyl,benzylamino or —NH—$(CH_2)_{n+1}N(R^{4"})_2$, and B is lower alkoxy, —O—$(CH_2)_{n+1}$-morpholinyl, —O—$(CH_2)_{n+1}$-piperidinyl or —O—$(CH_2)_{n+1}N(R^{4"})_2$;

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the NK, receptor was evaluated at human NK, receptors in CHO cells infected with the human $NK_1$ receptor (using the Semliki virus expression system) and radiolabelled with [³H]substance P (final concentration 0.6 nM). Binding assays were performed in HEPES buffer (50 mM, pH 7.4) containing BSA (0.04 %) leupeptin (8 µg/ml), $MnCl_2$ (3mM) and phosphoramidon (2 µM). Binding assays consisted of 250 µl of membrane suspension (1.25×10⁵ cells/assay tube), 0.125 µl of buffer of displacing agent and 125 µl of [³H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washed of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 8.00–9.30 for the preferred compounds. Examples of such compounds are

| | |
|---|---|
| 5-(2-chloro-phenyl)-2-(4-methyl-piperazin-1-yl)-pyrimidine-4-carboxylic acid (3,5-bis-trifluoromethyl-benzyl)-methyl-amide | 8.21 |
| 2-(2-dimethylamino-ethoxy)-5-o-tolyl-pyrimidine-4-carboxylic-acid (3,5-bis-trifluoromethyl-benzyl)-methyl-amide | 8.66 |
| 2-(4-methyl-piperazin-1-yl)-5-naphthalen-1-yl-pyrimidine-4-carboxylic acid (3,5-bis-trifluoromethyl-benzyl)-methyl-amide | 8.43 |
| 2-(2-dimethylamino-ethylamino)-5-(4-fluoro-2-methyl-phenyl)-pyrimidine-4-carboxylic acid (3,5-bis-trifluoromethyl-benzyl)-methyl-amide | 8.84 |
| 2-(3,5-bis-trifluoromethyl-phenyl)-N-[2-(2-dimethylamino-ethoxy)-5-o-tolyl-pyrimidin-4-yl]-N-methyl-isobutyramide | 9.18 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary. Preferred are dosages of 20 mg to 500 mg per day. Further preferred are dosages of 50 mg to 200 mg per day.

The following Examples illustrate the present invention without limiting it. All temperatures are given in degrees Celsius.

EXAMPLE 1

2-Methylsulfanyl-5-phenyl-pyrimidine-4-carboxylic acid (3,5-bis-trifluoromethyl-benzyl)-methyl-amide a) 5-Bromo-2-methylsulfanyl-pyrimidine-4-carboxylic acid 3,5-bis-trifluoromethyl-benzylamide To a solution of 3.54 g (14.21 mmol) 5-bromo-2-methylsulfanyl-pyrimidine-4-carboxylic 3.92 ml (28.24 mmol) triethylamin, 2.17 g (14.21 mmol) 1-hydroxybenzotriazol and 2.72 g (14.21 mmol) N-(3-dimethylaminopropyl)-N'-ethylcarbodiimide hydrochloride acid in 200 ml $CH_2Cl_2$ 3.80 g (15.63 mmol) 3,5-bis-trifluormethyl-benzylamin were added. The reaction mixture was stirred for 16 hrs. The reaction mixture was washed with 100 ml 0.5N HCl and 100 ml $H_2O$. The aqueous layers were backextracted with 100 ml $CH_2Cl_2$. The combined organic layers were dried ($MgSO_4$), filtered and evaporated. The residue was purified by chromatography ($SiO_2$, $CH_2Cl_2$) to give 4.70 g (69%) 5-bromo-2-methylsulfanyl-pyrimidine-4-carboxylic acid 3,5-bis-trifluoromethyl-benzylamide as a colorless solid.

b) 5-Bromo-2-methylsulfanyl-pyrimidine-4-carboxylic acid (3,5-bis-trifluoromethyl-benzyl)-methyl-amide To a solution of 4.40 g (9.28 mmol) 5-bromo-2-methylsulfanyl-pyrimidine-4-carboxylic acid 3,5-bis-trifluoromethyl-benzylamide in 50 ml N,N-dimethylformamide 0.48 g (12.06 mmol) sodiumhydride (60% dispersion in mineral oil) was added and the reaction mixture stirred for 1 hr. After the addition of 0.92 ml (14.85 mmol) methyl iodide at 0°, the reaction mixture was stirred for 3 hrs. at RT. The reaction mixture was distributed between 100 ml $H_2O$, 100 ml brine and 100 ml $CH_2Cl_2$. The phases were separated, the aqueous layer washed twice with 100 ml $CH_2Cl_2$. The combined organic layers were dried ($MgSO_4$), filtered and evaporated. The residue was purified by chromatography ($SiO_2$, $CH_2Cl_2$/ethyl acetate 40:1) to give 3.50 g (77%) 5-bromo-2-methylsulfanyl-pyrimidine-4-carboxylic acid (3,5-bis-trifluoromethyl-benzyl)-methyl-amide as a colorless oil.

c) 2-Methylsulfanyl-5-phenyl-pyrimidine-4-carboxylic acid (3,5-bis-trifluoromethyl-benzyl)-methyl-amide To a suspension of 3.50 g (7.17 mmol) 5-bromo-2-methylsulfanyl-pyrimidine-4-carboxylic acid (3,5-bistrifluoromethyl-benzyl)-methyl-amide, 0.213 g (0.2 mmol) tetrakis-(triphenylphosphin)palladium and 0.96 g (7.89 mmol) phenylboronic acid in 40 ml 1,2-dimethoxyethane a solution of 0.83 g (7.89 mmol) $Na_2CO_3$ in 15 ml $H_2O$ was added. The resulting reaction mixture was heated at reflux for 16 hrs. After evaporation of the 1,2-dimethoxyethan, the aqueous phase was extracted twice with 50 ml $CH_2Cl_2$. The combined organic layers were dried ($MgSO_4$), filtered and evaporated. The residue was purified by chromatography ($SiO_2$, $CH_2Cl_2$/ethyl acetate 40:1) and crystallised to give 2.4 g (69%) 2-methylsulfanyl-5-phenyl-pyrimidine-4-carboxylic acid (3,5-bis-trifluoromethyl-benzyl)-methyl-amide as off-white crystalls, m.p 109.7–110.7°.

EXAMPLE 2

2-Methanesulfonyl-5-phenyl-pyrimidine-4-carboxylic acid (3,5-bis-trifluoromethyl-benzyl)-methyl-amide To a solution of 2.30 g (4.74 mmol) 2-methylsulfanyl-5-phenyl-pyrimidine-4-carboxylic acid (3,5-bis-trifluoromethyl-benzyl)-methyl-amide in 90 ml $CH_2Cl_2$ 2.92 g (11.4 mmol) 3-chloroperbenzoic acid (70%) was added at 5° and the reaction mixture stirred for 3 hrs. at RT. After addition of 100 ml sat. $NaHCO_3$ solution, the layers were separated, the organic phase washed with sat. $NaHCO_3$-solution, dried ($Na_2SO_4$), filtered and evaporated. The residue was purified by chromatography ($SiO_2$, $CH_2Cl_2$/methanol 40:1) to give 2.30 g (94%) 2-methanesulfonyl-5-phenyl-pyrimidine-4-carboxylic acid (3,5-bis-trifluoromethyl-benzyl)-methyl-amide as a colorless solid, MS (EI): 517 ($M^+$).

EXAMPLE 3

2-Morpholin-4-yl-5-phenyl-pyrimidine-4-carboxylic acid (3,5-bis-trifluoromethyl-benzyl)-methyl-amide To a solution of 0.3 g (0.58 mmol) 2-methanesulfonyl-5-phenyl-pyrimidine-4-carboxylic acid (3,5-bis-trifluoromethyl-benzyl)-methyl-amide in 10 ml dioxan 0.12 ml (1.45 mmol) morpholine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/ethyl acetate 9:1) to give 0.16 g (53%) 2-morpholin-4-yl-5-phenyl-pyrimidine-4-carboxylic acid (3,5-bis-trifluoromethyl-benzyl)-methyl-amide as a off-white solid, m.p. 154.0–155.0°.

EXAMPLE 4

2-Benzylamino-5-phenyl-pyrimidine-4-carboxylic acid (3,5-bis-trifluoromethyl-benzyl)-methyl-amide To a solution of 0.3 g (0.58 mmol) 2-methanesulfonyl-5-phenyl-pyrimidine-4-carboxylic acid (3,5-bis-trifluoromethyl-benzyl)-methyl-amide in 10 ml dioxan 0.16 ml (1.45 mmol) benzylamine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/methanol 50:1) to give 0.14 g (44%) 2-benzylamino-5-phenyl-pyrimidine-4-carboxylic acid (3,5-bis-trifluoromethyl-benzyl)-methyl-amide as a off-white solid, m.p. 128.5–129.5°.

EXAMPLE 5

2-(4-Methyl-piperazin-1-yl)-5-phenyl-pyrimidine-4-carboxylic acid (3,5-bis-trifluoromethyl-benzyl)-methyl-amide To a solution of 0.3 g (0.58 mmol) 2-methanesulfonyl-5-phenyl-pyrimidine-4-carboxylic acid (3,5-bis-trifluoromethyl-benzyl)-methyl-amide in 10 ml dioxan 0.16 ml (1.45 mmol) 1-methyl-piperazine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 140:10:1) to give 0.15 g (48%) 2-(4-methyl-piperazin-1-yl)-5-phenyl-pyrimidine-4-carboxylic acid (3,5-bis-trifluoromethyl-benzyl)-methyl-amide as a off-white solid, m.p. 162.0–162.8°.

EXAMPLE 6

2-(2-Dimethylamino-ethylamino)-5-phenyl-pyrimidine-4-carboxylic acid (3,5-bis-trifluoromethyl-benzyl)-methyl-amide To a solution of 0.3 g (0.58 mmol) 2-methanesulfonyl-5-phenyl-pyrimidine-4-carboxylic acid (3,5-bis-trifluoromethyl-benzyl)-methyl-amide in 10 ml dioxan 0.16 ml (1.45 mmol) 2-dimethylaminoethylamin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 130:10:1) to give 0.05 g (16%) 2-(2-dimethylamino-ethylamino)-5-phenyl-pyrimidine-4-carboxylic acid (3,5-bis-trifluoromethyl-benzyl)-methyl-amide as a off-white solid, m.p. 108.5–109.5°.

EXAMPLE 7

2-Hydroxy-5-phenyl-pyrimidine-4-carboxylic acid (3,5-bis-trifluoromethyl-benzyl)-methyl-amide To a solution of 0.3 g (0.58 mmol) 2-methanesulfonyl-5-phenyl-pyrimidine-4-carboxylic acid (3,5-bis-trifluoromethyl-benzyl)-methyl-amide in 10 ml dioxan/$H_2O$ 5 ml 2N NaOH solution was added. The reaction mixture was stirred for 3 hrs. The pH of the reaction solution was than adjusted to 4 with 25% HCl. The aqueous layer was extracted three times with 50 ml $CH_2Cl_2$, the combined organic layers dried ($MgSO_4$), filtered and evaporated. The residue was purified by chromatography ($SiO_2$, $CH_2Cl_2$/methanol 9:1) to give 0.20 g (75%) 2-hydroxy-5-phenyl-pyrimidine-4-carboxylic acid (3,5-bis-trifluoromethyl-benzyl)-methyl-amide as a off-white solid, m.p. 218.5–219.5°.

EXAMPLE 8

2-Amino-5-phenyl-pyrimidine-4-carboxylic acid (3,5-bis-trifluoromethyl-benzyl)-methyl-amide To a solution of 0.3 g (0.58 mmol) 2-methanesulfonyl-5-phenyl-pyrimidine-4-carboxylic acid (3,5-bistrifluoromethyl-benzyl)-methyl-amide in 20 ml N,N-dimethylformamide a stream of $NH_3$-Gas was introduced during 10 Min. The reaction mixture was poured onto 100 ml $H_2O$. The aqueous layer was extracted three times with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 140:10:1) to give 0.17 g (65%) 2-amino-5-phenyl-pyrimidine-4-carboxylic acid (3,5-bis-trifluoromethyl-benzyl)-methyl-amide as a off-white solid, m.p. 181.5–182.5°.

EXAMPLE 9

2-Methoxy-5-phenyl-pyrimidine-4-carboxylic acid (3,5-bis-trifluoromethyl-benzyl)-methyl-amide To a solution of 0.45 g (0.87 mmol) 2-methanesulfonyl-5-phenyl-pyrimidine-4-carboxylic acid (3,5-bis-trifluoromethyl-benzyl)-methyl-amide in 15 ml methanol 0.123 g (2.17 mmol) sodiummethanolate (95%) were added at RT and the reaction solution stirred for 12 hrs. The reaction mixture was distibuted between 100 ml $H_2O$ and 100 ml $CH_2Cl_2$. The aqueous layer was extracted three times with 50 ml $CH_2Cl_2$, the combined organic layers dried ($MgSO_4$), filtered and evaporated. The residue was purified by chromatography ($SiO_2$, $CH_2Cl_2$/methanol 40:1) to give 0.30 g (73%) 2-methoxy-5-phenyl-pyrimidine-4-carboxylic acid (3,5-bis-trifluoromethyl-benzyl)-methyl-amide as a off-white solid, m.p. 97.5–98.5°.

EXAMPLE 10

2-Methyl-5-phenyl-pyrimidine-4-carboxylic acid (3,5-bis-trifluoromethyl-benzyl)-methyl-amide a) 5-Bromo-2-methyl-pyrimidine-4-carboxylic acid 3,5-bis-trifluoromethyl-benzylamide To a solution of 2.17 g (10 mmol) 5-Bromo-2-methyl-pyrimidine-4-carboxylic acid 3.18 ml (24 mmol) triethylamin, 1.62 g (12 mmol) 1-hydroxy-benzotriazol and 1.91 g (12 mmol) N-(3-dimethylaminopropyl)-N'-ethylcarbodiimide hydrochloride in 100 ml $CH_2Cl_2$ 2.91 g (12 mmol) 3,5-bis-trifluormethyl-benzylamin were added. The reaction mixture was stirred for 16 hrs. The reaction mixture was washed with 100 ml 0.5N HCl and 100 ml $H_2O$. The aqueous layers were backextracted with 100 ml $CH_2Cl_2$. The combined organic layers were dried ($MgSO_4$), filtered and evaporated. The residue was purified by chromatography ($SiO_2$, $CH_2Cl_2$) to give 2.95 g (67%) 5-bromo-2-methyl-pyrimidine-4-carboxylic acid 3,5-bis-trifluoromethyl-benzylamide as a pale yellow solid.

b) 5-Bromo-2-methyl-pyrimidine-4-carboxylic acid (3,5-bis-trifluoromethyl-benzyl)-methyl-amide To a solution of 2.28 g (5 mmol) 5-bromo-2-methyl-pyrimidine-4-carboxylic acid 3,5-bis-trifluoromethyl-benzylamide in 20 ml N,N-dimethylformamide 0.26 g (5.5 mmol) sodiumhydride (60% dispersion in mineral oil) was added and the reaction mixture stirred for 1 hr. After the addition of 0.4 ml (6.5 mmol) methyl iodide at 0°, the reaction mixture was stirred for 3 hrs. at RT. The reaction mixture was distributed between 80 ml $H_2O$, 80 ml brine and 80 ml $CH_2Cl_2$. The phases were separated, the aqueous layer washed twice with 80 ml $CH_2Cl_2$. The combined organic layers were dried ($MgSO_4$), filtered and evaporated. The residue was purified by chromatography ($SiO_2$, $CH_2Cl_2$/MeOH 19:1) to give 1.98 g (87%) 5-bromo-2-methyl-pyrimidine-4-carboxylic acid (3,5-bis-trifluoromethyl-benzyl)-methyl-amide as a waxy solid.

c) 2-Methyl-5-phenyl-pyrimidine-4-carboxylic acid (3,5-bis-trifluoromethyl-benzyl)-methyl-amide To a suspension of 0.456 g (1 mmol) 5-bromo-2-methyl-pyrimidine-4-carboxylic acid (3,5-bis-trifluoromethyl-benzyl)-methyl-amide, 0.034 g (0.2 mmol) tetrakis-(triphenylphosphin)palladium and 0.121 g (1 mmol) phenylboronic acid in 20 ml 1,2-dimethoxyethane a solution of 0.105 g (1 mmol) $Na_2CO_3$ in 8 ml $H_2O$ was added. The resulting reaction mixture was heated at reflux for 16 hrs. After evaporation of the 1,2-dimethoxyethan, the aqueous phase was extracted twice with 50 ml $CH_2Cl_2$. The combined organic layers were dried ($MgSO_4$), filtered and evaporated. The residue was purified by chromatography ($SiO_2$, $CH_2Cl_2$/MeOH 40:1) and crystallised (Ethanol) to give 0.258 g (57%) 2-methyl-5-phenyl-pyrimidine-4-carboxylic acid (3,5-bis-trifluoromethyl-benzyl)-methyl-amide as off-white crystals, m.p. 149–152°.

EXAMPLE 11

5-(2-Chloro-phenyl)-2-methylsulfanyl-pyrimidine-4-carboxylic acid (3,5-bis-trifluoromethyl-benzyl)-methyl-amide a) 5-(2-Chloro-phenyl)-2-methylsulfanyl-pyrimidine-4-carboxylic acid ethyl ester To a solution of 3.20 g (11.55 mmol) 5-bromo-2-methylsulfanyl-pyrimidine-4-carboxylic acid ethyl ester in 40 ml N,N-dimethylformamid 2.70 g (17.32 mmol) 2-chloro-phenyl-boronic acid, 4.82 ml (34.64 mmol) triethylamin, 0.077 g (0.35 mmol) palladium(II)acetate and 0.167 g (0.72 mmol) triphenylphosphin were added and the resulting reaction mixture heated for 4 hrs. at 105°. The reaction mixture was evaporated and the residue dissolved in 100 ml $CH_2Cl_2$. The organic phase was washed with 80 ml 0.5 N NaOH-Solution, 80 ml $H_2O$ and 80 ml brine. The organic phase was dried ($MgSO_4$), filtered and evaporated. The residue was purified by chromatography ($SiO_2$, $CH_2Cl_2$) to give 3.00 g (84%) 5-(2-chloro-phenyl)-2-methylsulfanyl-pyrimidine-4-carboxylic acid ethyl ester a as pale brown oil.

b) 5-(2-Chloro-phenyl)-2-methylsulfanyl-pyrimidine-4-carboxylic acid

To a solution of 3.00 g (9.72 mmol) 5-(2-chloro-phenyl)-2-methylsulfanyl-pyrimidine-4-carboxylic acid ethyl ester in 15 ml ethanol a solution of 0.58 g (14.5 mmol) NaOH in 15 ml was added at RT and the reaction solution was stirred for 1 hr. The pH of the solution was than adjusted to 1 by addition of 25% HCl. The resulting solution was extracted twice with 100 ml $CH_2Cl_2$/methanol (2:1). The combined organic phases were dried ($MgSO_4$), filtered and evaporated. The residue was suspended in 20 ml diisopropylether, filtered and dried to give 2.40 g (88%) 5-(2-chloro-phenyl)-2-methylsulfanyl-pyrimidine-4-carboxylic acid as an off-white solid.

c) 5-(2-Chloro-phenyl)-2-methylsulfanyl-pyrimidine-4-carboxylic acid (3,5-bis-trifluoromethyl-benzyl)-methyl-amide To a suspension of 2.40 g (8.55 mmol) 5-(2-chloro-phenyl)-2-methylsulfanyl-pyrimidine-4-carboxylic acid 2.38 ml (17.1 mmol) triethylamin, 1.30 g (8.55 mmol)

1-hydroxy-benzotriazol and 1.63 g (8.55 mmol) N-(3-dimethylaminopropyl)-N'-ethylcarbodiimide hydrochloride in 80 ml $CH_2Cl_2$ 2.41 g (8.55 mmol) (3,5-bis-trifluoromethyl-benzyl)-methyl-amine were added. The reaction mixture was stirred for 16 hrs. The reaction mixture was washed with 50 ml 0.5N HCl and 50 ml $H_2O$. The aqueous layers were backextracted with 50 ml $CH_2Cl_2$. The combined organic layers were dried ($MgSO_4$), filtered and evaporated. The residue was purified by chromatography ($SiO_2$, $CH_2Cl_2$) to give 3.80 g (85%) 5-(2-chloro-phenyl)-2-methylsulfanyl-pyrimidine-4-carboxylic acid (3,5-bis-trifluoromethyl-benzyl)-methyl-amide as a white foam, MS (ISP): 520.1 $(M+H)^+$.

EXAMPLE 12

5-(2-Chloro-phenyl)-2-methylsulfonyl-pyrimidine-4-carboxylic acid (3,5-bis-trifluoromethyl-benzyl)-methyl-amide To a solution of 3.70 g (7.12 mmol) 5-(2-chloro-phenyl)-2-methylsulfanyl-pyrimidine-4-carboxylic acid (3,5-bis-trifluoromethyl-benzyl)-methyl-amide in 100 ml $CH_2Cl_2$ 4.38 g (17.8 mmol) 3-chloroperbenzoic acid (70%) was added at 5° and the reaction mixture stirred for 2 hrs. at RT. The solution was washed with 80 ml sat. $NaHCO_3$-solution, 80 ml diluted $NaHSO_3$-solution and 80 ml $H_2O$. The organic phase was dried ($Na_2SO_4$), filtered and evaporated. The residue was purified by chromatography ($SiO_2$, $CH_2Cl_2$/MeOH 100:1) to give 3.10 g (97%) 5-(2-chloro-phenyl)-2-methylsulfonyl-pyrimidine-4-carboxylic acid (3,5-bis-trifluoromethyl-benzyl)-methyl-amide as a white foam, MS (ISP): 551.9 $(M+H)^+$.

EXAMPLE 13

5-(2-Chloro-phenyl)-2-(4-methyl-piperazin-1-yl)-pyrimidine-4-carboxylic acid (3,5-bis-trifluoromethyl-benzyl)-methyl-amide To a solution of 0.40 g (0.72 mmol) 5-(2-chloro-phenyl)-2-methylsulfonyl-pyrimidine-4-carboxylic acid (3,5-bis-trifluoromethyl-benzyl)-methyl-amide in 10 ml dioxan 0.20 ml (1.81 mmol) 1-methyl-piperazine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.37 g (89%) 5-(2-chloro-phenyl)-2-(4-methyl-piperazin-1-yl)-pyrimidine-4-carboxylic acid (3,5-bis-trifluoromethyl-benzyl)-methyl-amide as a white foam, MS (ISP): 572.1 $(M+H^+)$.

EXAMPLE 14

5-(2-Chloro-phenyl)-2-(2-dimethylamino-ethylamino)-pyrimidine-4-carboxylic acid (3,5-bis-trifluoromethyl-benzyl)-methyl-amide To a solution of 0.56 g (0.10 mmol) 5-(2-chloro-phenyl)-2-methylsulfonyl-pyrimidine-4-carboxylic acid (3,5-bis-trifluoromethyl-benzyl)-methyl-amide in 10 ml dioxan 0.27 ml (2.54 mmol) 2-dimethylaminoethylamin was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 140:10:1) to give 0.49 g (86%) 5-(2-chloro-phenyl)-2-(2-dimethylamino-ethylamino)-pyrimidine-4-carboxylic acid (3,5-bis-trifluoromethyl-benzyl)-methyl-amide as a white foam, MS (ISP): 560.2 $(M+H)^+$.

EXAMPLE 15

5-(2-Chloro-phenyl)-2-(3-dimethylamino-propoxy)-pyrimidine-4-carboxylic acid (3,5-bis-trifluoromethyl-benzyl)-methyl-amide To a solution of 0.5 g (0.91 mmol) 5-(2-chloro-phenyl)-2-methylsulfonyl-pyrimidine-4-carboxylic acid (3,5-bis-trifluoromethyl-benzyl)-methyl-amide in 20 ml acetonitrile 0.14 ml (1.18 mmol) 2-dimethylamino-propanol and 1.47 g (4.53 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.40 g (77%) 5-(2-chloro-phenyl)-2-(3-dimethylamino-propoxy)-pyrimidine-4-carboxylic acid (3,5-bis-trifluoromethyl-benzyl)-methyl-amide as a colorless oil, MS (ISP): 575.1 $(M+H)^+$.

EXAMPLE 16

5-(2-Chloro-phenyl)-2-(2-dimethylamino-ethoxy)-pyrimidine-4-carboxylic acid (3,5-bis-trifluoromethyl-benzyl)-methyl-amide To a solution of 0.50 g (0.91 mmol) 5-(2-chioro-phenyl)-2-methylsulfonyl-pyrimidine-4-carboxylic acid (3,5-bis-trifluoromethyl-benzyl)-methyl-amide in 20 ml acetonitrile 0.118 ml (1.18 mmol) 2-dimethylamino-ethanol and 1.47 g (4.53 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.40 g (77%) 5-(2-chloro-phenyl)-2-(3-dimethylamino-ethoxy)-pyrimidine-4-carboxylic acid (3,5-bis-trifluoromethyl-benzyl)-methyl-amide as a off-white solid, MS (ISP): 561.3 $(M+H)^+$.

EXAMPLE 17

5-(2-Chloro-phenyl)-2-(2-morpholin-4-yl-ethoxy)-pyrimidine-4-carboxylic acid (3,5-bis-trifluoromethyl-benzyl)-methyl-amid To a solution of 0.50 g (0.91 mmol) 5-(2-chloro-phenyl)-2-methylsulfonyl-pyrimidine-4-carboxylic acid (3,5-bis-trifluoromethyl-benzyl)-methyl-amide in 20 ml acetonitrile 0.143 ml (1.18 mmol) N-(2-hydroxyethyl)morpholine and 1.47 g (4.53 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 140:10:1) to give 0.40 g (73%) 5-(2-chloro-phenyl)-2-(2-morpholin-4-ylethoxy)-pyrimidine-4-carboxylic acid (3,5-bis-trifluoromethyl-benzyl)-methyl-amide as a off-white foam, MS (ISP): 603.0 (M+H)+.

EXAMPLE 18

2-Methylsulfanyl-5-o-tolyl-pyrimidine-4-carboxylic acid (3,5-bis-trifluoromethyl-benzyl)-methyl-amide In an analogus manner to that described in Example 11 a) there was obtained from 5-bromo-2-methylsulfanyl-pyrimidine-4-carboxylic acid ethyl ester and o-tolylboronic acid 2-methylsulfanyl-5-o-tolyl-pyrimidine-4-carboxylic acid ethyl ester, which was saponified as described in Example 11 b) and reacted with (3,5-bis-trifluoromethyl-benzyl)-methyl-amine to give as described in Example 11 c) 2-methylsulfanyl-5-o-tolyl-pyrimidine-4-carboxylic acid (3,5-bis-trifluoromethyl-benzyl)-methyl-amide as a white foam, MS (ISP): 500.2 (M+H)+.

EXAMPLE 19

2-Methanesulfonyl-5-o-tolyl-pyrimidine-4-carboxylic acid (3,5-bis-trifluoromethyl-benzyl)-methyl-amide In an analogous manner to that described in Example 12 there was obtained from 2-methylsulfanyl-5-o-tolyl-pyrimidine-4-carboxylic acid (3,5-bis-trifluoromethyl-benzyl)-methyl-amide and 3-chloroperbenzoic acid 2-methylsulfonyl-5-o-tolyl-pyrimidine-4-carboxylic acid (3,5-bis-trifluoromethyl-benzyl)-methyl-amide as a white foam, MS (EI): 531 (M+).

EXAMPLE 20

2-(2-Dimethylamino-ethylamino)-5-o-tolyl-pyrimidine-4-carboxylic acid (3,5-bis-trifluoromethyl-benzyl)-methyl-amide In an analogous manner to that described in Example 14 there was obtained from 2-methylsulfonyl-5-o-tolyl-pyrimidine-4-carboxylic acid (3,5-bis-trifluoromethyl-benzyl)-methyl-amide and 2-dimethylaminoethylamin 2-(2-dimethylamino-ethylamino)-5-o-tolyl-pyrimidine-4-carboxylici acid (3,5-bis-trifluoromethyl-benzyl)-methyl-amide as a white foam, MS (ISP): 540.3 (M+H)+.

EXAMPLE 21

2-(2-Dimethylamino-ethoxy)-5-o-tolyl-pyrimidine-4-carboxylic acid (3,5-bis-trifluoromethyl-benzyl)-methyl-amide In an analogous manner to that described in Example 16 there was obtained from 2-methylsulfonyl-5-o-tolyl-pyrimidine-4-carboxylic acid (3,5-bis-trifluoromethyl-benzyl)-methyl-amide and 2-dimethylamino-ethanol 2-(2-dimethylamino-ethoxy)-5-o-tolyl-pyrimidine-4-carboxylic acid (3,5-bis-trifluoromethyl-benzyl)-methyl-amide as a white foam, MS (ISP): 541.2 (M+H)+, which was treated with HCl in Ethanol in the in the usual way to give 2-(2-dimethylamino-ethoxy)-5-o-tolyl-pyrimidine-4-carboxylic acid (3,5-bis-trifluoromethyl-benzyl)-methyl-amide hydrochloride, m.p. 147–149°.

EXAMPLE 22

2-(3-Dimethylamino-propoxy)-5-o-tolyl-pyrimidine-4-carboxylic acid (3,5-bis-trifluoromethyl-benzyl)-methyl-amide In an analogous manner to that described in Example 15 there was obtained from 2-methylsulfonyl-5-o-tolyl-pyrimidine-4-carboxylic acid (3,5-bis-trifluoromethyl-benzyl)-methyl-amide and 2-dimethylamino-propanol 2-(2-dimethylamino-propoxy)-5-o-tolyl-pyrimidine-4-carboxylic acid (3,5-bis-trifluoromethyl-benzyl)-methyl-amide as a white foam, MS (ISP): 555.2 (M+H)+.

EXAMPLE 23

2-Methylsulfanyl-5-naphthalen-1-yl-pyrimidine-4-carboxylic acid (3,5-bis-trifluoromethyl-benzyl)-methyl-amide In an analogous manner to that described in Example 11 a) there was obtained from 2-bromo-5-methylsulfanyl-benzoic acid ethyl ester and 1-naphthylboronic acid 2-methylsulfanyl-5-naphthalen-1-yl-pyrimidine-4-carboxylic acid ethyl ester, which was saponified as described in Example 11 b) and reacted with (3,5-bis-trifluoromethyl-benzyl)-methyl-amine to give as described in Example 11 c) 2-methylsulfanyl-5-naphthalen-1-yl-pyrimidine-4-carboxylic acid (3,5-bis-trifluoromethyl-benzyl)-methyl-amide as a white foam, MS (EI): 535 (M+).

EXAMPLE 24

2-Methanesulfonyl-5-naphthalen-1-yl-pyrimidine-4-carboxylic acid (3,5-bis-trifluoromethyl-benzyl)-methyl-amide In an analogous manner to that described in Example 12 there was obtained from 2-methanesulfanyl-5-naphthalen-1-yl-pyrimidine-4-carboxylic acid (3,5-bis-trifluoromethyl-benzyl)-methyl-amide and 3-chloroperbenzoic acid 2-methanesulfonyl-5-naphthalen-1-yl-pyrimidine-4-carboxylic acid (3,5-bis-trifluoromethyl-benzyl)-methyl-amide as a white foam, MS (EI): 567 (M+).

EXAMPLE 25

2-(4-Methyl-piperazin-1-yl)-5-naphthalen-1-yl-pyrimidine-4-carboxylic acid (3,5-bis-trifluoromethyl-benzyl)-methyl-amide In an analogous manner to that described in Example 13 there was obtained from 2-methanesulfonyl-5-naphthalen-1-yl-pyrimidine-4-carboxylic acid (3,5-bis-trifluoromethyl-benzyl)-methyl-amide and 1-methyl-piperazin 2-(4-methyl-piperazin-1-yl)-5-naphthalen-1-yl-pyrimidine-4-carboxylic acid (3,5-bis-trifluoromethyl-benzyl)-methyl-amide as a white foam, MS (ISP): 588.2(M+H)+.

EXAMPLE 26

2-(2-Dimethylamino-ethylamino)-5-naphthalen-1-yl-pyrimidine-4-carboxylic acid (3,5-bis-trifluoromethyl-benzyl)-methyl-amide In an analogous manner to that described in Example 14 there was obtained from 2-methanesulfonyl-5-naphthalen-1-yl-pyrimidine-4-carboxylic acid (3,5-bis-trifluoromethyl-benzyl)-methyl-amide and 2-dimethylaminoethylamin 2-(2-dimethylamino-ethylamino)-5-naphthalen-1-yl-pyrimidine-4-carboxylic acid (3,5-bis-trifluoromethyl-benzyl)-methyl-amide as a white foam, MS (ISP): 576.2 (M+H)+.

EXAMPLE 27

2-(2-Dimethylamino-ethoxy)-5-naphthalen-1-yl-pyrimidine-4-carboxylic acid (3,5-bis-trifluoromethyl-benzyl)-methyl-amide In an analogous manner to that described in Example 16 there was obtained from 2-methanesulfonyl-5-naphthalen- 1-yl-pyrimidine-4-carboxylic acid (3,5-bis-trifluoromethyl-benzyl)-methyl-amide and 2-dimethylamino-ethanol 2-(2-dimethylamino-ethoxy)-5-naphthalen-1-yl-pyrimidine-4-carboxylic acid (3,5-bis-trifluoromethyl-benzyl)-methyl-amide as a white foam, MS (TSP): 576 (M$^+$).

EXAMPLE 28

2-(2-Morpholin-4-yl-ethoxy)-5-naphthalen-1-yl-pyrimidine-4-carboxylic acid (3,5-bis-trifluoromethyl-benzyl)-methyl-amide In an analogous manner to that described in Example 17 there was obtained from 2-methanesulfonyl-5-naphthalen-1-yl-pyrimidine-4-carboxylic acid (3,5-bis-trifluoromethyl-benzyl)-methyl-amide and N-(2-hydroxyethyl)morpholine 2-(2-morpholin-4-yl-ethoxy)-5-naphthalen-1-yl-pyrimidine-4-carboxylic acid (3,5-bis-trifluoromethyl-benzyl)-methyl-amide as a white foam, MS (ISP): 619.2 (M+H)$^+$.

EXAMPLE 29

2-(3-Dimethylamino-propoxy)-5-naphthalen-1-yl-pyrimidine-4-carboxylic acid (3,5-bis-trifluoromethyl-benzyl)-methyl-amide In an analogous manner to that described in Example 15 there was obtained from 2-methanesulfonyl-5-naphthalen-1-yl-pyrimidine-4-carboxylic acid (3,5-bis-trifluoromethyl-benzyl)-methyl-amide and 2-dimethylamino-propanol 2-(2-dimethylamino-propoxy)-5-naphthalen-1-yl-pyrimidine-4-carboxylic acid (3,5-bis-trifluoromethyl-benzyl)-methyl-amide as a white foam, MS (ISP): 591.1 (M+H)$^+$.

EXAMPLE 30

5-(2-Methoxy-phenyl)-2-methylsulfanyl-pyrimidine-4-carboxylic acid (3,5-bis-trifluoromethyl-benzyl)-methyl-amide In an analogous manner to that described in Example 11 a) there was obtained from 5-bromo-2-methylsulfanyl-pyrimidine-4-carboxylic acid ethyl ester and 2-methoxyphenyl boronic acid 5-(2-methoxy-phenyl)-2-methylsulfanyl-pyrimidine-4-carboxylic acid ethyl ester, which was saponified as described in Example 11 b) and reacted with (3,5-bis-trifluoromethyl-benzyl)-methyl-amine to give as described in Example 11 c) 5-(2-methoxy-phenyl)-2-methylsulfanyl-pyrimidine-4-carboxylic acid (3,5-bis-trifluoromethyl-benzyl)-methyl-amide, MS (EI): 515 (M$^+$).

EXAMPLE 31

2-Methanesulfonyl-5-(2-methoxy-phenyl)-pyrimidine-4-carboxylic acid (3,5-bis-trifluoromethyl-benzyl)-methyl-amide In an analogous manner to that described in Example 12 there was obtained from 2-methanesulfanyl-5-(2-methoxy-phenyl)-pyrimidine-4-carboxylic acid (3,5-bis-trifluoromethyl-benzyl)-methyl-amide and 3-chloroperbenzoic acid 2-methanesulfonyl-5-(2-methoxy-phenyl)-pyrimidine-4-carboxylic acid (3,5-bis-trifluoromethyl-benzyl)-methyl-amide as a white foam, MS (TSP): 547 (M$^+$).

EXAMPLE 32

2-(2-Dimethylamino-ethylamino)-5-(2-methoxy-phenyl)-pyrimidine-4-carboxylic acid (3,5-bis-trifluoromethyl-benzyl)-methyl-amide In an analogus manner to that described in Example 14 there was obtained from 2-methanesulfonyl-5-(2-methoxy-phenyl)-pyrimidine-4-carboxylic acid (3,5-bis-trifluoromethyl-benzyl)-methyl-amide and 2-dimethylaminoethylamin 2-(2-dimethylamino-ethylamino)-5-(2-methoxy-phenyl)-pyrimidine-4-carboxylic acid (3,5-bis-trifluoromethyl-benzyl)-methyl-amide as a white foam, MS (ISP): 556.1 (M+H)$^+$.

EXAMPLE 33

5-(2-Methoxy-phenyl)-2-(4-methyl-piperazin-1-yl)-pyrimidine-4-carboxylic acid (3,5-bis-rifluoromethyl-benzyl)-methyl-amide In an analogous manner to that described in Example 13 there was obtained from 2-methanesulfonyl-5-(2-methoxy-phenyl)-pyrimidine-4-carboxylic acid (3,5-bis-trifluoromethyl-benzyl)-methyl-amide and 1-methyl-piperazine 5-(2-methoxy-phenyl)-2-(4-methyl-piperazin-1-yl)-pyrimidine-4-carboxylic acid (3,5-bis-trifluoromethyl-benzyl)-methyl-amide as a white foam, MS (ISP): 557.2 (M+H)$^+$.

EXAMPLE 34

2-(2-Dimethylamino-ethoxy)-5-(2-methoxy-phenyl)-pyrimidine-4-carboxylic acid (3,5-bis-trifluoromethyl-benzyl)-methyl-amide In an analogous manner to that described in Example 16 there was obtained from 2-methanesulfonyl-5-(2-methoxy-phenyl)-pyrimidine-4-carboxylic acid (3,5-bis-trifluoromethyl-benzyl)-methyl-amide and 2-dimethylaminoethanol 2-(2-dimethylamino-ethoxy)-5-(2-methoxy-phenyl)-pyrimidine-4-carboxylic acid (3,5-bis-trifluoromethyl-benzyl)-methyl-amide as a white foam, MS (ISP): 557.2 (M+H)$^+$.

EXAMPLE 35

2-(2-Dimethylamino-propoxy)-5-(2-methoxy-phenyl)-pyrimidine-4-carboxylic acid (3,5-bis-trifluoromethyl-benzyl)-methyl-amide In an analogous manner to that described in Example 15 there was obtained from 2-methanesulfonyl-5-(2-methoxy-phenyl)-pyrimidine-4-carboxylic acid (3,5-bis-trifluoromethyl-benzyl)-methyl-amide and 2-dimethylaminopropanol 2-(2-dimethylamino-propoxy)-5-(2-methoxy-phenyl)-pyrimidine-4-carboxylic acid (3,5-bis-trifluoromethyl-benzyl)-methyl-amide as a white foam, MS (ISP): 571.1 (M+H)$^+$.

EXAMPLE 36

5-(2-Methoxy-phenyl)-2-(2-morpholin-4-yl-ethoxy)-pyrimidine-4-carboxylic acid (3,5-bis-trifluoromethyl-benzyl)-methyl-amide In an analogous manner to that described in Example 17 there was obtained from 2-methanesulfonyl-5-(2-methoxy-phenyl)-pyrimidine-4-carboxylic acid (3,5-bis-trifluoromethyl-benzyl)-methyl-amide and N-(2-hydroxyethyl)morpholine 5-(2-methoxy-phenyl)-2-(2-morpholin-4-yl-ethoxy)-pyrimidine-4-carboxylic acid (3,5-bis-trifluoromethyl-benzyl)-methyl-amide as a white foam, MS (ISP): 599.1 (M+H)$^+$.

EXAMPLE 37

2-Methylsulfanyl-5-naphthalen-2-yl-pyrimidine-4-carboxylic acid (3,5-bis-trifluoromethyl-benzyl)-methyl-amide In an analogus manner to that described in Example 11 a) there was obtained from 5-bromo-2-methylsulfanylpyrimidine-4-carboxylic acid ethyl ester and 2-naphthylboronic acid 2-methylsulfanyl-5-naphthalen-2-yl-pyrimidine-4-carboxylic acid ethyl ester, which was saponified as described in Example 11 b) and reacted with (3,5-bis-trifluoromethyl-benzyl)-methyl-amine to give as described in Example 11 c) 2-methylsulfanyl-5-naphthalen-2-yl-pyrimidine-4-carboxylic acid (3,5-bis-trifluoromethyl-benzyl)-methyl-amide as a white foam, MS (ISP): 536.2 (M+H)$^+$.

EXAMPLE 38

2-Methanesulfonyl-5-naphthalen-2-yl-pyrimidine-4-carboxylic acid (3,5-bis-trifluoromethyl-benzyl)-methyl-amide In an analogous manner to that described in Example 12 there was obtained from 2-methanesulfanyl-5-naphthalen-2-yl-pyrimidine-4-carboxylic acid (3,5-bis-trifluoromethyl-benzyl)-methyl-amide and 3-chloroperbenzoic acid 2-methanesulfonyl-5-naphthalen-2-yl-pyrimidine-4-carboxylic acid (3,5-bis-trifluoromethyl-benzyl)-methyl-amide as a white foam, MS (TSP): 567(M$^+$).

EXAMPLE 39

2-(4-Methyl-piperazin-1-yl)-5-naphthalen-2-yl-pyrimidine-4-carboxylic acid (3,5-bis-trifluoromethyl-benzyl)-methyl-amide In an analogous manner to that described in Example 13 there was obtained from 2-methanesulfonyl-5-naphthalen-2-yl-pyrimidine-4-carboxylic acid (3,5-bis-trifluoromethyl-benzyl)-methyl-amide and 1-methylpiperazine 2-(4-methyl-piperazin-1-yl)-5-naphthalen-2-yl-pyrimidine-4-carboxylic acid (3,5-bis-trifluoromethyl-benzyl)-methyl-amide as a white foam, MS (ISP): 588.3 (M+H)$^+$.

EXAMPLE 40

2-(2-Dimethylamino-ethylamino)-5-naphthalen-2-yl-pyrimidine-4-carboxylic acid (3,5-bis-trifluoromethyl-benzyl)-methyl-amide In an analogous manner to that described in Example 14 there was obtained from 2-methanesulfonyl-5-naphthalen-2-yl-pyrimidine-4-carboxylic acid (3,5-bis-trifluoromethyl-benzyl)-methyl-amide and 2-dimethylaminoethylamin 2-(2-dimethylamino-ethylamino)-5-naphthalen-2-yl-pyrimidine-4-carboxylic acid (3,5-bis-trifluoromethyl-benzyl)-methyl-amide as a white foam, MS (ISP): 576.1 (M+H)$^+$.

EXAMPLE 41

2-(2-Dimethylamino-ethoxy)-5-naphthalen-2-yl-pyrimidine-4-carboxylic acid (3,5-bis-trifluoromethyl-benzyl)-methyl-amide In an analogous manner to that described in Example 16 there was obtained from 2-methanesulfonyl-5-naphthalen-2-yl-pyrimidine-4-carboxylic acid (3,5-bis-trifluoromethyl-benzyl)-methyl-amide and 2-dimethylaminoethanol 2-(2-dimethylamino-ethoxy)-5-naphthalen-2-yl-pyrimidine-4-carboxylic acid (3,5-bis-trifluoromethyl-benzyl)-methyl-amide as a white foam, MS (ISP): 577.1 (M+H)$^+$.

EXAMPLE 42

5-(4-Fluoro-phenyl)-2-methylsulfanyl-pyrimidine-4-carboxylic acid (3,5-bis-trifluoromethyl-benzyl)-methyl-amide In an analogus manner to that described in Example 11 a) there was obtained from 5-bromo-2-methylsulfanyl-pyrimidine-4-carboxylic acid ethyl ester and 4-fluorboronic acid 5-(4-fluoro-phenyl)-2-methylsulfanyl-pyrimidine-4-carboxylic acid ethyl ester, which was saponified as described in Example 11 b) and reacted with (3,5-bis-trifluoromethyl-benzyl)-methyl-amine to give as described in Example 11 c) 5-(4-fluoro-phenyl)-2-methylsulfanyl-pyrimidine-4-carboxylic acid (3,5-bis-trifluoromethyl-benzyl)-methyl-amide as a white foam, MS (EI): 503 (M$^+$).

EXAMPLE 43

5-(4-Fluoro-phenyl)-2-methylsulfonyl-pyrimidine-4-carboxylic acid (3,5-bis-trifluoromethyl-benzyl)-methyl-amide In an analogous manner to that described in Example 12 there was obtained from 5-(4-fluoro-phenyl)-2-methylsulfanyl-pyrimidine-4-carboxylic acid (3,5-bis-trifluoromethyl-benzyl)-methyl-amide and 3-chloroperbenzoic acid 5-(4-fluoro-phenyl)-2-methylsulfonyl-pyrimidine-4-carboxylic acid (3,5-bis-trifluoromethyl-benzyl)-methyl-amide as a white foam, MS (EI): 535 (M$^+$).

EXAMPLE 44

2-(3-Dimethylamino-propoxy)-5-(4-fluoro-phenyl)-pyrimidine-4-carboxylic acid (3,5-bis-trifluoromethyl-benzyl)-methyl-amide In an analogous manner to that described in Example 15 there was obtained from 5-(4-fluoro-phenyl)-2-methylsulfonyl-pyrimidine-4-carboxylic acid (3,5-bis-trifluoromethyl-benzyl)-methyl-amide and 2-dimethylaminopropanol 2-(3-dimethylamino-propoxy)-5-(4-fluoro-phenyl)-pyrimidine-4-carboxylic acid (3,5-bis-trifluoromethyl-benzyl)-methyl-amide as a white foam, MS (ISP): 559.3 (M+H)$^+$.

EXAMPLE 45

2-(2-Dimethylamino-ethoxy)-5-(4-fluoro-phenyl)-pyrimidine-4-carboxylic acid (3,5-bis-trifluoromethyl-benzyl)-methyl-amide In an analogous manner to that described in Example 16 there was obtained from 5-(4-fluoro-phenyl)-2-methylsulfonyl-pyrimidine-4-carboxylic acid (3,5-bis-trifluoromethyl-benzyl)-methyl-amide and 2-dimethylaminoethanol 2-(3-dimethylamino-ethoxy)-5-(4-fluoro-phenyl)-pyrimidine-4-carboxylic acid (3,5-bis-trifluoromethyl-benzyl)-methyl-amide as a white foam, MS (ISP): 545.2 (M+H)$^+$.

EXAMPLE 46

2-(2-Dimethylamino-ethylamino)-5-(4-fluoro-phenyl)-pyrimidine-4-carboxylic acid (3,5-bis-trifluoromethyl-benzyl)-methyl-amide In an analogous manner to that described in Example 14 there was obtained from 5-(4-fluoro-phenyl)-2-methylsulfonyl-pyrimidine-4-carboxylic acid (3,5-bis-trifluoromethyl-benzyl)-methyl-amide and 2-dimethylaminoethylamin 2-(3-dimethylamino-ethylamino)-5-(4-fluoro-phenyl)-pyrimidine-4-carboxylic acid (3,5-bis-trifluoromethyl-benzyl)-methyl-amide as a white foam, MS (ISP): 544.2 (M+H)$^+$.

EXAMPLE 47

5-(4-Fluoro-phenyl)-2-(2-morpholin-4-yl-ethoxy)-pyrimidine-4-carboxylic acid (3,5-bis-trifluoromethyl-benzyl)-methyl-amide In an analogous manner to that described in Example 17 there was obtained from 5-(4-fluoro-phenyl)-2- methylsulfonyl-pyrimidine-4-carboxylic acid (3,5-bis-trifluoromethyl-benzyl)-methyl-amide and N-(2-hydroxyethyl)morpholine 5-(4-fluoro-phenyl)-2-(2-morpholin-4-yl-ethoxy)-pyrimidine-4-carboxylic acid (3,5-bis-trifluoromethyl-benzyl)-methyl-amide as a white foam, MS (ISP): 587.2 (M+H)$^+$.

EXAMPLE 48

5-(4-Fluoro-2-methyl-phenyl)-2-methylsulfanyl-pyrimidine-4-carboxylic acid (3,5-bis-trifluoromethyl-benzyl)-methyl-amide In an analogus manner to that described in Example 11 a) there was obtained from 5-bromo-2-methylsulfanyl-pyrimidine-4-carboxylic acid ethyl ester and 4-fluoro-2-methyl-phenyl boronic acid 5-(4-fluoro-2-methyl-phenyl)-2-methylsulfanyl-pyrimidine-4-carboxylic acid ethyl ester, which was saponified as described in Example 11 b) and reacted with (3,5-bis-trifluoromethyl-benzyl)-methyl-amine to give as described in Example 11 c) 5-(4-fluoro-2-methyl-phenyl)-2-methylsulfanyl-pyrimidine-4-carboxylic acid (3,5-bis-trifluoromethyl-benzyl)-methyl-amide as a white foam, MS (EI): 517 (M$^+$).

EXAMPLE 49

5-(4-Fluoro-2-methyl-phenyl)-2-methylsulfonyl-pyrimidine-4-carboxylic acid (3,5-bis-trifluoromethyl-benzyl)-methyl-amide In an analogous manner to that described in Example 12 there was obtained from 5-(4-fluoro-2-methyl-phenyl)-2-methylsulfanyl-pyrimidine-4-carboxylic acid (3,5-bis-trifluoromethyl-benzyl)-methyl-amide and 3-chloroperbenzoic acid 5-(4-fluoro-2-methyl-phenyl)-2-methylsulfonyl-pyrimidine-4-carboxylic acid (3,5-bis-trifluoromethyl-benzyl)-methyl-amide as a white foam, MS (EI): 549 (M$^+$).

EXAMPLE 50

5-(4-Fluoro-2-methyl-phenyl)-2-(2-morpholin-4-yl-ethoxy)-pyrimidine-4-carboxylic acid (3,5-bis-trifluoromethyl-benzyl)-methyl-amide In an analogous manner to that described in Example 17 there was obtained from 5-(4-fluoro-2-methyl-phenyl)-2-methylsulfonyl-pyrimidine-4-carboxylic acid (3,5-bis-trifluoromethyl-benzyl)-methyl-amide and N-(2-hydroxyethyl)morpholine 5-(4-fluoro-2-methyl-phenyl)-2-(2-morpholin-4-yl-ethoxy)-pyrimidine-4-carboxylic acid (3,5-bis-trifluoromethyl-benzyl)-methyl-amide as a white foam, MS (ISP): 601.1 (M+H)$^+$.

EXAMPLE 51

2-(3-Dimethylamino-propoxy)-5-(4-fluoro-2-methyl-phenyl)-pyrimidine-4-carboxylic acid (3,5-bis-trifluoromethyl-benzyl)-methyl-amide In an analogous manner to that described in Example 15 there was obtained from 5-(4-fluoro-2-methyl-phenyl)-2-methylsulfonyl-pyrimidine-4-carboxylic acid (3,5-bis-trifluoromethyl-benzyl)-methyl-amide and 2-dimethylaminopropanol 2-(3-dimethylamino-propoxy)-5-(4-fluoro-2-methyl-phenyl)-pyrimidine-4-carboxylic acid (3,5-bis-trifluoromethyl-benzyl)-methyl-amide as a white foam, MS (ISP): 573.1 (M+H)$^+$.

EXAMPLE 52

2-(2-Dimethylamino-ethoxy)-5-(4-fluoro-2-methyl-phenyl)-pyrimidine-4-carboxylic acid (3,5-bis-trifluoromethyl-benzyl)-methyl-amide In an analogous manner to that described in Example 16 there was obtained from 5-(4-fluoro-2-methyl-phenyl)-2-methylsulfonyl-pyrimidine-4-carboxylic acid (3,5-bis-trifluoromethyl-benzyl)-methyl-amide and 2-dimethylaminoethanol 2-(3-dimethylamino-ethoxy)-5-(4-fluoro-2-methyl-phenyl)-pyrimidine-4-carboxylic acid (3,5-bis-trifluoromethyl-benzyl)-methyl-amide as a white foam, MS (ISP): 559.2 (M+H)$^+$.

EXAMPLE 53

5-(4-Fluoro-2-methyl-phenyl)-2-(4-methyl-piperazin-1-yl)-pyrimidine-4-carboxylic acid (3,5-bis-trifluoromethyl-benzyl)-methyl-amide In an analogous manner to that described in Example 13 there was obtained from 5-(4-fluoro-2-methyl-phenyl)-2-methylsulfonyl-pyrimidine-4-carboxylic acid (3,5-bis-trifluoromethyl-benzyl)-methyl-amide and 1-methyl-piperazine 5-(4-fluoro-2-methyl-phenyl)-2-(4-methyl-piperazin-1-yl)-pyrimidine-4-carboxylic acid (3,5-bis-trifluoromethyl-benzyl)-methyl-amide as a white foam, MS (ISP): 570.2 (M+H)$^+$.

EXAMPLE 54

2-(2-Dimethylamino-ethylamino)-5-(4-fluoro-2-methyl-phenyl)-pyrimidine-4-carboxylic acid (3,5-bis-trifluoromethyl-benzyl)-methyl-amide In an analogous manner to that described in Example 14 there was obtained from 5-(4-fluoro-2-methyl-phenyl)-2-methylsulfonyl-pyrimidine-4-carboxylic acid (3,5-bis-trifluoromethyl-benzyl)-methyl-amide and 2-dimethylaminoethylamin 2-(2-dimethylamino-ethylamino)-5-(4-fluoro-2-methyl-phenyl)-pyrimidine-4-carboxylic acid (3,5-bis-trifluoromethyl-benzyl)-methyl-amide as a white foam, MS (ISP): 558.3 (M+H)$^+$.

EXAMPLE 55

5-(2-Chloro-phenyl)-2-hydroxymethyl-pyrimidine-4-carboxylic acid (3,5-bis-trifluoromethyl-benzyl)-methyl-amide a) 5-Bromo-2-hydroxymethyl-pyrimidine-4-carboxylic acid ethyl ester A solution of 4.2 g (18.02 mmol) 5-bromo-2-hydroxymethyl-pyrimidine-4-carboxylic acid in 50 ml 5N HCl/EtOH was stirred for 5 hrs. at RT. After evaporation of the solvent the residue was distributed between 50 ml CH$_2$Cl$_2$ and 30 ml H$_2$O. The organic phase was washed with sat. NaHCO$_3$ and brine. The combined organic phases were dried (Na$_2$SO$_4$), filtered and evaporated. The residue was purified by chromatography to give 3.80 g (80%) 5-bromo-2-hydroxymethyl-pyrimidine-4-carboxylic acid ethyl ester as a pale yellow solid.

b) 5-(2-Chloro-phenyl)-2-hydroxymethyl-pyrimidine-4-carboxylic acid ethyl ester

To a solution of 3.70 g (14.17 mmol) 5-bromo-2-hydroxymethyl-pyrimidine-4-carboxylic acid ethyl ester in 50 ml N,N-dimethylformamide 3.32 g (21.6 mmol) 2-chloro-phenyl-boronic acid, 5.92 ml (42.52 mmol) triethylamine, 0.095 g (0.43 mmol) palladium(II)acetate and 0.223 g (0.85 mmol) triphenylphosphine were added and the resulting reaction mixture heated for 4 hrs. at 105°. The reaction mixture was evaporated and the residue dissolved in 100 ml CH$_2$Cl$_2$. The organic phase was washed with 80 ml 0.5 N NaOH-Solution, 80 ml H$_2$O and 80 ml brine. The organic phase was dried (MgSO$_4$), filtered and evaporated. The residue was purified by chromatography (SiO$_2$, CH$_2$Cl$_2$/ethyl acetate) to give 3.40 g (82%) 5-(2-chloro-phenyl)-2-hydroxymethyl-pyrimidine-4-carboxylic acid ethyl ester a as pale brown oil.

c) 5-(2-Chloro-phenyl)-2-hydroxymethyl-pyrimidine-4-carboxylic acid

To a solution of 3.40 g (11.6 mmol) (2-chloro-phenyl)-2-hydroxymethyl-pyrimidine-4-carboxylic acid ethyl ester in 15 ml ethanol 0.69 g (17.42 mmol) NaOH in 15 ml H$_2$O was added and the mixture stirred for 1 hr. The pH of the solution was adjusted to 1 and the solid was filtered off to give after drying 2.80 g (91%) 5-(2-chloro-phenyl)-2-hydroxymethyl-pyrimidine-4-carboxylic acid as a pale brown solid.

d) 5-(2-Chloro-phenyl)-2-hydroxymethyl-pyrimidine-4-carboxylic acid (3,5-bis-trifluoromethyl-benzyl)-methyl-amide To a suspension of 2.80 g (10.58 mmol) 5-(2-chloro-phenyl)-2-hydroxymethyl-pyrimidine-4-carboxylic acid in 70 ml CH$_2$Cl$_2$ 2.94 ml (21.2 mmol) triethylamin, 1.62 g (10.58 mmol) 1-hydroxy-benzotriazol and 2.02 g (10.58 mmol) N-(3-dimethylaminopropyl)-N'-ethylcarbodiimide hydrochloride 2.99 g (11.64 mmol) (3,5-bis-trifluoromethyl-benzyl)-methyl-amine were added. The reaction mixture was stirred for 16 hrs. The reaction mixture was washed with 50 ml 0.5N HCl and 50 ml H$_2$O. The aqueous layers were back extracted with 50 ml CH$_2$Cl$_2$. The combined organic layers were dried (MgSO$_4$), filtered and evaporated. The residue was purified by chromatography (SiO$_2$, CH$_2$Cl$_2$/MeOH 19:1) to give 3.80 g (71%) 5-(2-chloro-phenyl)-2-hydroxymethyl-pyrimidine-4-carboxylic acid (3,5-bis-trifluoromethyl-benzyl)-methyl-amide as a pale brown oil, MS (ISP): 504.2 (M+H$^+$).

EXAMPLE 56

5-(2-Chloro-phenyl)-2-(4-methyl-piperazin-1-ylmethyl)-pyrimidine-4-carboxylic acid (3,5-bis-trifluoromethyl-benzyl)-methyl-amide a) Methanesulfonic acid 4-[(3,5-bis-trifluoromethyl-benzyl)-methyl-carbamoyl]-5-(2-chloro-phenyl)-pyrimidin-2-ylmethyl ester and 2-Chloromethyl-5-(2-chloro-phenyl)-pyrimidine-4-carboxylic acid (3.5-bis-trifluoromethyl-benzyl)-methyl-amide To a solution of 3.80 g (7.54 mmol) 5-(2-chloro-phenyl)-2-hydroxymethyl-pyrimidine-4-carboxylic acid (3,5-bis-trifluoromethyl-benzyl)-methyl-amide and 1.57 ml (11.31 mmol) triethylamine in 80 ml CH$_2$Cl$_2$ 0.645 ml (8.30 mmol) methansulfonylchloride were added at 0°. The reaction mixture was stirred for 16 hrs. The reaction mixture was poured onto sat. NaHCO$_3$-solution and extracted three times with 50 ml CH$_2$Cl$_2$. The combined organic layers were dried (MgSO$_4$), filtered and evaporated. The residue was purified by chromatography (SiO$_2$, CH$_2$Cl$_2$/ethyl acetate 8:1) to give 2.70 g (61%) methanesulfonic acid 4-[(3,5-bis-trifluoromethyl-benzyl)-methyl-carbamoyl]-5-(2-chloro-phenyl)-pyrimidin-2-ylmethyl ester as a pale brown oil, MS (ISP): 582.0 (M+H$^+$) and 0.90 g (22%) 2-chloromethyl-5-(2-chloro-phenyl)-pyrimidine-4-carboxylic acid (3,5-bis-trifluoromethyl-benzyl)-methyl-amide as a pale brown oil, MS (ISP): 522.1 (M+H$^+$).

b) 5-(2-Chloro-phenyl)-2-(4-methyl-piperazin-1-ylmethyl)-pyrimidine-4-carboxylic acid (3,5-bis-trifluoromethyl-benzyl)-methyl-amide To a solution of 0.39 g (0.75 mmol) 2-chloromethyl-5-(2-chloro-phenyl)-pyrimidine-4-carboxylic acid (3,5-bis-trifluoromethyl-benzyl)-methyl-amide in 10 ml CH$_2$Cl$_2$ 0.20 ml (1.87 mmol) N-methylpiperazine were added. The reaction mixture was stirred for 16 hrs. at RT and than poured into H$_2$O and extracted three times with 50 ml CH$_2$Cl$_2$. The combined organic layers were dried (MgSO$_4$), filtered and evaporated. The residue was purified by chromatography (SiO$_2$, CH$_2$Cl$_2$/MeOH/NH$_4$OH 110:10:1) to give 0.27 g (61%) 5-(2-chloro-phenyl)-2-(4-methyl-piperazin-1-ylmethyl)-pyrimidine-4-carboxylic acid (3,5-bis-trifluoromethyl-benzyl)-methyl-amide as a colorless oil, MS (ISP): 586.1 (M+H$^+$).

EXAMPLE 57

5-(2-Chloro-phenyl)-2-morpholin-4-ylmethyl-pyrimidine-4-carboxylic acid (3,5-bis-trifluoromethyl-benzyl)-methyl-amide To a solution of 0.58 g (1.11 mmol) 2-chloromethyl-5-(2-chloro-phenyl)-pyrimidine-4-carboxylic acid (3,5-bis-trifluoromethyl-benzyl)-methyl-amide in 10 ml CH$_2$Cl$_2$ 0.24 ml (2.78 mmol) morpholine were added. The reaction mixture was stirred for 16 hrs. at RT and than poured into H$_2$O and extracted three times with 50 ml CH$_2$Cl$_2$. The combined organic layers were dried (MgSO$_4$), filtered and evaporated. The residue was purified by chromatography (SiO$_2$, CH$_2$Cl$_2$/MeOH/NH$_4$OH 200:10:1) to give 0.40 g (62%) 5-(2-chloro-phenyl)-2-morpholin-4-ylmethyl-pyrimidine-4-carboxylic acid (3,5-bis-trifluoromethyl-benzyl)-methyl-amide as a colorless foam, MS (ISP): 573.1 (M+H$^+$).

EXAMPLE 58

5-(2-Chloro-phenyl)-2-[(2-dimethylamino-ethylamino)-methyl]-pyrimidine-4-carboxylic acid (3,5-bis-trifluoromethyl-benzyl)-methyl-amide To a solution of 0.62 g (1.07 mmol) methanesulfonic acid 4-[(3,5-bis-trifluoromethyl-benzyl)-methyl-carbamoyl]-5-(2-chloro-phenyl)-pyrimidin-2-ylmethyl ester in 10 ml CH$_2$Cl$_2$ 0.29 ml (2.66 mmol) 2-dimethylyminoethylamine were added. The reaction mixture was stirred for 16 hrs. at RT and than poured into H$_2$O and extracted three times with 50 ml CH$_2$Cl$_2$. The combined organic layers were dried (MgSO$_4$), filtered and evaporated. The residue was purified by chromatography (SiO$_2$, CH$_2$Cl$_2$/MeOH/NH$_4$OH 110:10:1) to give 0.22 g (36%) 5-(2-chloro-phenyl)-2-[(2-dimethylamino-ethylamino)-methyl]-pyrimidine-4-carboxylic acid (3,5-bis-trifluoromethyl-benzyl)-methyl-amide as a colorless oil, MS (ISP): 574.1 (M+H$^+$).

EXAMPLE 59

5-(2-Chloro-phenyl)-2-dimethylaminomethyl-pyrimidine-4-carboxylic acid (3,5-bis-trifluoromethyl-benzyl)-methyl-amide To a solution of 0.62 g (1.07 mmol) methanesulfonic acid 4-[(3,5-bis-trifluoromethyl-benzyl)-methyl-carbamoyl]-5-(2-chloro-phenyl)-pyrimidin-2-ylmethyl ester in 10 ml CH$_2$Cl$_2$ 1.53 ml (8.52 mmol) of a 5.6 M solution of dimethylamine were added. The reaction mixture was stirred for 16 hrs. at RT and than poured into H$_2$O and extracted three times with 50 ml CH$_2$Cl$_2$. The combined organic layers were dried (MgSO$_4$), filtered and evaporated. The residue was purified by chromatography (SiO$_2$, CH$_2$Cl$_2$/MeOH/NH$_4$OH 200:10:1) to give 0.40 g (70%) 5-(2-chloro-phenyl)-2-dimethylaminomethyl-pyrimidine-4-carboxylic acid (3,5-bis-trifluoromethyl-benzyl)-methyl-amide as a colorless oil, MS (ISP): 531.1 (M+H$^+$).

Example 60

2-Methylsulfanyl-5-o-tolyl-pyrimidine-4-carboxylic acid (3,5-dimethyl-benzyl)-methyl-amide To a suspension of 0.30 g (1.15 mmol) 2-methylsulfanyl-5-o-tolyl-pyrimidine-4-carboxylic acid in 20 ml $CH_2Cl_2$, 0.32 ml (2.3 mmol) triethylamine, 0.17 g (1.15 mmol) 1-hydroxy-benzotriazole and 0.22 g (1.15 mmol) N-(3-dimethylaminopropyl)-N'-ethylcarbodiimide hydrochloride 0.20 g (1.38 mmol) (3,5-dimethyl-benzyl)-methyl-amine were added. The reaction mixture was stirred for 16 hrs. The reaction mixture was washed with 50 ml 0.5N HCl and 50 ml $H_2O$. The aqueous layers were back extracted with 50 ml $CH_2Cl_2$. The combined organic layers were dried ($MgSO_4$), filtered and evaporated. The residue was purified by chromatography ($SiO_2$, $CH_2Cl_2$) to give 0.36 g (79%) 2-methylsulfanyl-5-o-tolyl-pyrimidine-4-carboxylic acid (3,5-dimethyl-benzyl)-methyl-amide as a white foam, MS (EI): 391 ($M^+$).

EXAMPLE 61

2-Methanesulfonyl-5-o-tolyl-pyrimidine-4-carboxylic acid (3,5-dimethyl-benzyl)-methyl-amide To a solution of 0.36 g (0.92 mmol) 2-methylsulfanyl-5-o-tolyl-pyrimidine-4-carboxylic acid (3,5-dimethyl-benzyl)-methyl-amide in 20 ml $CH_2Cl_2$ 0.56 g (0.23 mmol) 3-chloroperbenzoic acid (70%) was added at 5° and the reaction mixture stirred for 3 hrs. at RT. After addition of 50 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/MeOH 40:1) to give 0.29 g (74%) 2-methanesulfonyl-5-o-tolyl-pyrimidine-4-carboxylic acid (3,5-dimethyl-benzyl)-methyl-amide as a colorless foam, MS (EI): 423 ($M^+$).

EXAMPLE 62

2-(4-Methyl-piperazin-1-yl)-5-o-tolyl-pyrimidine-4-carboxylic acid (3,5-dimethyl-benzyl)-methyl-amide To a solution of 0.28 g (0.66 mmol) 2-methanesulfonyl-5-o-tolyl-pyrimidine-4-carboxylic acid (3,5-dimethyl-benzyl)-methyl-amide in 10 ml dioxane 0.18 ml (1.65 mmol) 1-methylpiperazine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.18 g (61%) 2-(4-methyl-piperazin-1-yl)-5-o-tolyl-pyrimidine-4-carboxylic acid (3,5-dimethyl-benzyl)-methyl-amide as a colorless foam, MS (ISP): 444.5 ($M+H^+$).

EXAMPLE 63

2-Morpholin-4-yl-5-o-tolyl-pyrimidine-4-carboxylic acid (3,5-dimethyl-benzyl)-methyl-amide To a solution of 0.21 g (0.49 mmol) 2-methanesulfonyl-5-o-tolyl-pyrimidine-4-carboxylic acid (3,5-dimethyl-benzyl)-methyl-amide in 10 ml dioxane 0.13 ml (1.48 mmol) morpholine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH 100:1) to give 0.17 g (78%) 2-morpholin-4-yl-5-o-tolyl-pyrimidine-4-carboxylic acid (3,5-dimethyl-benzyl)-methyl-amide as a colorless foam, MS (ISP): 431.5 ($M+H^+$).

EXAMPLE 64

2-Methylsulfanyl-5-o-tolyl-pyrimidine-4-carboxylic acid (3,5-dimethoxy-benzyl)-methyl-amide To a suspension of 0.30 g (1.15 mmol) 2-methylsulfanyl-5-o-tolyl-pyrimidine-4-carboxylic acid in 20 ml $CH_2Cl_2$, 0.32 ml (2.3 mmol) triethylamine, 0.17 g (1.15 mmol) 1-hydroxy-benzotriazole and 0.22 g (1.15 mmol) N-(3-dimethylaminopropyl)-N'-ethylcarbodiimide hydrochloride 0.25 g (1.38 mmol) (3,5-dimethoxy-benzyl)-methyl-amine were added. The reaction mixture was stirred for 16 hrs. The reaction mixture was washed with 50 ml 0.5N HCl and 50 ml $H_2O$. The aqueous layers were back extracted with 50 ml $CH_2Cl_2$. The combined organic layers were dried ($MgSO_4$), filtered and evaporated. The residue was purified by chromatography ($SiO_2$, $CH_2Cl_2$/MeOH 40:1) to give 0.45 g (92%) 2-methylsulfanyl-5-o-tolyl-pyrimidine-4-carboxylic acid (3,5-dimethyoxy-benzyl)-methyl-amide as a white foam, MS (EI): 423 ($M^+$).

EXAMPLE 65

2-Methanesulfonyl-5-o-tolyl-pyrimidine-4-carboxylic acid (3,5-dimethoxy-benzyl)-methyl-amide To a solution of 0.45 g (1.06 mmol) 2-methylsulfanyl-5-o-tolyl-pyrimidine-4-carboxylic acid (3,5-dimethyoxy-benzyl)-methyl-amide in 20 ml $CH_2Cl_2$ 0.65 g (0.26 mmol) 3-chloroperbenzoic acid (70%) was added at 5° and the reaction mixture stirred for 3 hrs. at RT. After addition of 50 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/MeOH 40:1) to give 0.20 g (41%) 2-methanesulfonyl-5-o-tolyl-pyrimidine-4-carboxylic acid (3,5-dimethyoxy-benzyl)-methyl-amide as a colorless foam, MS (EI): 455 ($M^+$).

EXAMPLE 66

2-(4-Methyl-piperazin-1-yl)-5-o-tolyl-pyrimidine-4-carboxylic acid (3,5-dimethoxy-benzyl)-methyl-amide To a solution of 0.18 g (0.4 mmol) 2-methanesulfonyl-5-o-tolyl-pyrimidine-4-carboxylic acid (3,5-dimethoxy-benzyl)-methyl-amide in 10 ml dioxane 0.11 ml (0.99 mmol) 1-methylpiperazine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.16 g (85%) 2-(4-methyl-piperazin-1-yl)-5-o-tolyl-pyrimidine-4-carboxylic acid (3,5-dimethoxy-benzyl)-methyl-amide as a colorless foam, MS (ISP): 476.3 ($M+H^+$).

EXAMPLE 67

2-Methylsulfanyl-5-o-tolyl-pyrimidine-4-carboxylic acid 3,5-dichloro-benzylamide To a solution of 1.2 g (4.6 mmol) 2-methylsulfanyl-5-o-tolyl-pyrimidine-4-carboxylic acid in 30 ml $CH_2Cl_2$ 1.28 ml (9.2 mmol) triethylamine, 0.62 g (4.6 mmol) 1-hydroxybenzotriazole and 0.88 g (4.6 mmol) N-(3-dimethylaminopropyl)-N'-ethylcarbodiimide hydrochloride 1.05 g (6 mmol) 3,5-dichlorobenzylamine were added. The reaction mixture was stirred for 16 hrs. The reaction mixture was diluted with 20 ml $CH_2Cl_2$, washed with 50 ml 0.5N HCl and 50 ml $H_2O$. The aqueous layers were back extracted with 50 ml $CH_2Cl_2$. The combined organic layers were dried ($MgSO_4$), filtered and evaporated. The residue was purified by chromatography ($SiO_2$, $CH_2Cl_2$/MeOH 100:1) to give 1.64 g (85%) 2-methylsulfanyl-5-o-tolyl-pyrimidine-4-carboxylic acid 3,5-dichloro-benzylamide as a colorless foam, MS (ISP): 418.1, 420.1 (M+H$^+$).

EXAMPLE 68

2-Methanesulfonyl-5-o-tolyl-pyrimidine-4-carboxylic acid 3,5-dichloro-benzylamide To a solution of 0.3 g (0.71 mmol) methylsulfanyl-5-o-tolyl-pyrimidine-4-carboxylic acid 3,5-dichloro-benzylamide in 25 ml $CH_2Cl_2$ 0.44 g (1.79 mmol) 3-chloroperbenzoic acid (70%) was added at 5° and the reaction mixture stirred for 3 hrs. at RT. After addition of 20 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/MeOH 125:1) to give 0.305 g (94%) 2-methanesulfonyl-5-o-tolyl-pyrimidine-4-carboxylic acid 3,5-dichloro-benzylamide as a colorless foam, MS (ISP): 450.2,452.2 (M+H$^+$).

EXAMPLE 69

2-(4-Methyl-piperazin-1-yl)-5-o-tolyl-pyrimidine-4-carboxylic acid 3,5-dichloro-benzylamide To a solution of 0.19 g (0.435 mmol) 2-methanesulfonyl-5-o-tolyl-pyrimidine-4-carboxylic acid 3,5-dichloro-benzylamide in 5 ml dioxane 0.12 ml (1.08 mmol) 1-methylpiperazine was added. The reaction mixture was stirred for 16 hrs. After evaporation of the solvent, the residue was distributed between 5 ml $CH_2Cl_2$ and 25 ml $H_2O$. The aqueous layer was extracted with 20 ml $CH_2Cl_2$, the combined organic layers were dried ($MgSO_4$), filtered and evaporated. The residue was purified by chromatography ($SiO_2$, $CH_2Cl_2$/MeOH 9:1) to give 0.18 g (88%) 2-(4-methyl-piperazin-1-yl)-5-o-tolyl-pyrimidine-4-carboxylic acid 3,5-dichloro-benzylamide as a colorless oil, MS (ISP): 470.2, 472.2 (M+H$^+$).

EXAMPLE 70

2-Methylsulfanyl-5-o-tolyl-pyrimidine-4-carboxylic acid (3,5-dichloro-benzyl)-methyl-amide To a solution of 0.6 g (1.43 mmol) methylsulfanyl-5-o-tolyl-pyrimidine-4-carboxylic acid 3,5-dichloro-benzylamide in 10 ml N,N-dimethylformamide 0.073 g (1.85 mmol) sodiumhydride (60% dispersion in mineral oil) was added and the reaction stirred for 1 h. After the addition of 0.14 ml methyl iodide at 0°, the reaction mixture was stirred for 3 hrs at RT. The reaction mixture was distributed between 50 ml $H_2O$, 50 ml brine and 50 ml $CH_2Cl_2$. The phases were separated and the aqueous layer washed twice with 50 ml $CH_2Cl_2$. The combined organic layers were dried ($MgSO_4$), filtered and evaporated. The residue was purified by chromatography ($SiO_2$, $CH_2Cl_2$/ethyl acetate 40:1) to give 0.57 g (92%) 2-methylsulfanyl-5-o-tolyl-pyrimidine-4-carboxylic acid (3,5-dichloro-benzyl)-methyl-amide as a colorless oil, MS (ISP): 432.2, 434.2 (M+H$^+$).

EXAMPLE 71

2-Methylsulfonyl-5-o-tolyl-pyrimidine-4-carboxylic acid (3,5-dichloro-benzyl)-methyl-amide To a solution of 0.57 g (1.31 mmol) methylsulfanyl-5-o-tolyl-pyrimidine-4-carboxylic acid (3,5-dichloro-benzyl)-methyl-amide in 50 ml $CH_2Cl_2$ 0.81 g (3.29 mmol) 3-chloroperbenzoic acid (70%) was added at 50 and the reaction mixture stirred for 3 hrs. at RT. After addition of 40 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/MeOH 100:1) to give 0.58 g (94%) 2-methylsulfonyl-5-o-tolyl-pyrimidine-4-carboxylic acid (3,5-dichloro-benzyl)-methyl-amide as a colorless foam, MS (EI): 463, 465 (M$^+$).

EXAMPLE 72

2-(4-Methyl-piperazin-1-yl)-5-o-tolyl-pyrimidine-4-carboxylic acid (3,5-dichloro-benzyl)-methyl-amide To a solution of 0.25 g (0.538 mmol) 2-methylsulfonyl-5-o-tolyl-pyrimidine-4-carboxylic acid (3,5-dichloro-benzyl)-methyl-amide in 5 ml dioxane 0.15 ml (1.34 mmol) 1-methylpiperazine was added. The reaction mixture was stirred for 16 hrs. After evaporation of the solvent, the residue was distributed between 25 ml $CH_2Cl_2$ and 25 ml $H_2O$. The aqueous layer was extracted with 20 ml $CH_2Cl_2$, the combined organic layers dried ($MgSO_4$), filtered and evaporated. The residue was purified by chromatography ($SiO_2$, $CH_2Cl_2$/MeOH/$NH_4OH$) 9:1) to give 0.116 g (44%) 2-(4-methyl-piperazin-1-yl)-5-o-tolyl-pyrimidine-4-carboxylic acid (3,5-dichloro-benzyl)-methyl-amide as a colorless oil, MS (ISP): 484.3, 486.3 (M+H$^+$).

EXAMPLE 73

2-(3,5-Bis-trifluoromethyl-phenyl)-N-methyl-N-(2-methylsulfanyl-5-o-tolyl-pyrimidin-4-yl)-isobutyramide a) (2-Methylsulfanyl-5-o-tolyl-pyrimidin-4-yl)-carbamic acid tert.-butyl ester To a solution of 2.29 g (8.8 mmol) 2-methylsulfanyl-5-o-tolyl-pyrimidine-4-carboxylic acid, 1.26 ml triethylamine (8.8 mmol) and 1.66 ml (17.6 mmol) butyl alcohol in 30 ml THF, 1.90 ml (8.8 mmol) diphenylphosphorylazide were added and the resulting solution heated at reflux for 12 hrs. After evaporation of the solvent, the residue was distributed between $CH_2Cl_2$ and $H_2O$. The aqueous phase was extracted twice with $CH_2Cl_2$. The combined organic layers were dried ($Na_2SO_4$), filtered and evaporated. The residue was purified by chromatography ($SiO_2$, $CH_2Cl_2$/ethyl acetate 19:1) to give 2.45 g (84%) (2-methylsulfanyl-5-o-tolyl-pyrimidin-4-yl)-carbamic acid ter.-butyl ester as a colorless solid, MS (TSP): 331 (M$^+$).

b) Methyl-(2-methylsulfanyl-5-o-tolyl-pyrimidin-4-yl)-carbamic acid tert.-butyl ester To a solution of 2.45 g (7.40 mmol) (2-methylsulfanyl-5-o-tolyl-pyrimidin-4-yl)-carbamic acid tert.-butyl ester in 30 ml N,N-dimethylformamide 0.44 g (11.09 mmol) sodiumhydride (60% dispersion in mineraloil) was added and the reaction mixture stirred for 1 hr. After the addition of 0.74 ml (11.83 mmol) methyl iodide at 0°, the reaction mixture was stirred for 3 hrs. The reaction mixture was distributed between 75 ml H$_2$O, 75 ml brine and 75 ml CH$_2$Cl$_2$. The phases were separated, the aqueous layer washed twice with 75 ml CH$_2$Cl$_2$. The combined organic layers were dried (Na$_2$SO$_4$), filtered and evaporated. The residue was purified by chromatography (SiO$_2$, CH$_2$Cl$_2$/ethyl acetate 19:1) to give 2.50 g (98%) methyl-(2-methylsulfanyl-5-o-tolyl-pyrimidin-4-yl)-carbamic acid tert.-butyl ester as a colorless oil, MS (TSP): 345 (M$^+$).

c) Methyl-(2-methylsulfanyl-5-o-tolyl-pyrimidin-4-yl)-amine

A solution of 2.66 g (7.7 mmol) methyl-(2-methylsulfanyl-5-o-tolyl-pyrimidin-4-yl)-carbamic acid tert-butyl ester in 30 ml MeOH/HCl (2N) was stirred at 50° for 3 hr. After evaporation of the solvent, the residue was distributed between 40 ml 1N NaOH and 40 ml CH$_2$Cl$_2$. The phases were separated, the aqueous layer washed twice with 50 ml CH$_2$Cl$_2$. The combined organic layers were dried (Na$_2$SO$_4$), filtered and evaporated. The residue was purified by chromatography (SiO$_2$, CH$_2$Cl$_2$) to give 1.48 g (78%) methyl-(2-methylsulfanyl-4-o-tolyl-pyrimidin-5-yl)-amine as a white solid, MS (EI): 245 (M$^+$).

d) 2-(3,5-Bis-trifluoromethyl-phenyl)-N-methyl-N-(2-methylsulfanyl-5-o-tolyl-pyrimidin-4-yl)-isobutyramide To a solution of 1.48 g (6.0 mmol) methyl-(2-methylsulfanyl-4-o-tolyl-pyrimidin-5-yl)-amine in 10 ml N,N-dimethylformamide 6.4 ml of a 1M solution potassiumhexamethyldisilazide (6.4 mmol) in THF were added at 0°. After 1 h, 2.3 g (7.22 mmol) (2-(3,5-bis-trifluoromethyl-phenyl)-2-methyl-propionyl chloride in 5 ml THF were added and the reaction mixture stirred for 24 hrs. at RT. The reaction mixture was poured onto 50 ml 0.5 N NaOH-solution. After addition of ethyl acetate the phases were separated, the aqueous layer washed twice with 50 ml ethyl acetate. The combined organic layers were dried (Na$_2$SO$_4$), filtered and evaporated. The residue was purified by chromatography (SiO$_2$, CH$_2$Cl$_2$/ethyl acetate 10:1) to give 1.20 g (37 %) 2-(3,5-bis-trifluoromethyl-phenyl)-N-methyl-N-(2-methylsulfanyl-5-o-tolyl-pyrimidin-4-yl)-isobutyramide as a white foam, MS (ISP): 528.2 (M+H$^+$).

EXAMPLE 74

2-(3,5-Bis-trifluoromethyl-phenyl)-N-(2-methanesulfonyl-5-o-tolyl-pyrimidin-4-yl)-N-methyl-isobutyramide To a solution of 1.20 g (2.27 mmol) 2-(3,5-bis-trifluoromethyl-phenyl)-N-methyl-N-(2-methylsulfanyl-5-o-tolyl-pyrimidin-4-yl)-isobutyramide in 50 ml CH$_2$Cl$_2$ 1.46 g (5.91 mmol) 3-chloroperbenzoic acid (70%) was added at 5° and the reaction mixture stirred for 3 hrs. at RT. After addition of 100 ml sat. NaHCO$_3$-solution, the layers were separated, the organic phase washed with sat. NaHCO$_3$-solution, dried (Na$_2$SO$_4$), filtered and evaporated. The residue was purified by chromatography (SiO$_2$, CH$_2$Cl$_2$) to give 1.10 g (86%) 2-(3,5-bis-trifluoromethyl-phenyl)-N-(2-methanesulfonyl-5-o-tolyl-pyrimidin-4-yl)-N-methyl-isobutyramide as a colorless foam, MS (EI): 559 (M+H$^+$).

EXAMPLE 75

2-(3,5-Bis-trifluoromethyl-phenyl)-N-methyl-N-[2-(4-methyl-piperazin-1-yl)-5-o-tolyl-pyrimidin-4-yl]-isobutyramide To a solution of 0.2 g (0.36 mmol) 2-(3,5-bis-trifluoromethyl-phenyl)-N-(2-methanesulfonyl-5-o-tolyl-pyrimidin-4-yl)-N-methyl-isobutyramide in 10 ml dioxan 0.09 ml (0.89 mmol) 1-methylpiperazine was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH/NH$_4$OH 140:10:1) to give 0.08 g (36%) 2-(3,5-bis-trifluoromethyl-phenyl)-N-methyl-N-[2-(4-methyl-piperazin-1-yl)-5-o-tolyl-pyrimidin-4-yl]-isobutyramide as a colorless foam, MS (ISP): 580.1 (M+H$^+$).

EXAMPLE 76

2-(3,5-Bis-trifluoromethyl-phenyl)-N-methyl-N-(2-piperazin-1-yl-5-o-tolyl-pyrimidin-4-yl)-isobutyramide To a solution of 0.2 g (0.36 mmol) 2-(3,5-bis-trifluoromethyl-phenyl)-N-(2-methanesulfonyl-5-o-tolyl-pyrimidin-4-yl)-N-methyl-isobutyramide in 10 ml dioxane 0.1 g (0.89 mmol) piperazine was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH/NH$_4$OH 110:10:1) to give 0.18 g (89%) 2-(3,5-bis-trifluoromethyl-phenyl)-N-methyl-N-(2-piperazin-1-yl-5-o-tolyl-pyrimidin-4-yl)-isobutyramide as a colorless foam, MS (ISP):556.2 (M+H$^+$).

EXAMPLE 77

2-(3,5-Bis-trifluoromethyl-phenyl)-N-methyl-N-(2-morpholin-4-yl-5-o-tolyl-pyrimidin-4-yl)-isobutyramide To a solution of 0.2 g (0.36 mmol) 2-(3,5-bis-trifluoromethyl-phenyl)-N-(2-methanesulfonyl-5-o-tolyl-pyrimidin-4-yl)-N-methyl-isobutyramide in 10 ml dioxane 0.08 g (0.89 mmol) morpholine was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH 90:1) to give 0.18 g (89%) 2-(3,5-bis-trifluoromethyl-phenyl)-N-methyl-N-(2-morpholin-4-yl-5-o-tolyl-pyrimidin-4-yl)-isobutyramide as a colorless foam, MS (ISP): 567.2 (M+H$^+$).

EXAMPLE 78

2-(3,5-Bis-trifluoromethyl-phenyl)-N-[2-(2-dimethylamino-ethylamino)-5-o-tolyl-pyrimidin-4-yl]-N-methyl-isobutyramide To a solution 0.2 g (0.36 mmol) 2-(3,5-bis-trifluoromethyl-phenyl)-N-(2-methanesulfonyl-5-o-tolyl-pyrimidin-4-yl)-N-methyl-isobutyramide in 10 ml dioxan 0.09 ml (0.89 mmol) 2-dimethylaminoethylamin was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH/NH$_4$OH 140:10:1) to give 0.15 g (77%) 2-(3,5-bis-trifluoromethyl-phenyl)-N-[2-(2-dimethylamino-ethylamino)-5-o-tolyl-pyrimidin-4-yl]-N-methyl-isobutyramide as a colorless foam, MS (ISP): 568.3 (M+H$^+$).

EXAMPLE 79

2-(3,5-Bis-trifluoromethyl-phenyl)-N-[2-(2-dimethylamino-ethoxy)-5-o-tolyl-pyrimidin-4-yl]-N-methyl-isobutyramide To a solution of 0.3 g (0.54 mmol) 2-(3,5-bis-trifluoromethyl-phenyl)-N-(2-methanesulfonyl-5-o-tolyl-pyrimidin-4-yl)-N-methyl-isobutyramide in 10 ml acetonitrile 0.08 ml (0.8 mmol) 2-dimethylamino-ethanol and 0.97 g (2.68 mmol) Cs$_2$CO$_3$ were added. The reaction mixture was stirred for 16 hrs. After evaporation of the solvent, the residue was distributed between 40 ml CH$_2$Cl$_2$ and 40 ml H$_2$O. The aqueous layer was extracted with 40 ml CH$_2$Cl$_2$, the combined organic layers dried (MgSO$_4$), filtered and evaporated. The residue was purified by chromatography (SiO$_2$, CH$_2$Cl$_2$/MeOH/NH$_4$OH 140:10:1) to give 0.27 g (88%) 2-(3,5-bis-trifluoromethyl-phenyl)-N-[2-(2-dimethylamino-ethoxy)-5-o-tolyl-pyrimidin-4-yl]-N-methyl-isobutyramide as a colorless solid, MS (ISP): 569.2 (M+H$^+$).

EXAMPLE 80

2-(3,5-Bis-trifluoromethyl-phenyl)-N-[5-(2-chloro-phenyl)-2-methylsulfanyl-pyrimidin-4-yl]-N-methyl-isobutyramide a) [5-(2-Chloro-phenyl)-2-methylsulfanyl-pyrimidin-4-yl]-carbamic acid tert.-butyl ester To a solution of 2.50 g (8.9 mmol) 5-(2-chloro-phenyl)-2-methylsulfanyl-pyrimidine-4-carboxylic acid, 1.24 ml triethylamine (8.9 mmol) and 1.67 ml (17.8 mmol) butyl alcohol in 30 ml THF, 1.91 ml (8.9 mmol) diphenylphosphorylazide were added and the resulting solution heated at reflux for 12 hrs. After evaporation of the solvent, the residue was distributed between CH$_2$Cl$_2$ and H$_2$O. The aqueous phase was extracted twice with CH$_2$Cl$_2$. The combined organic layers were dried (Na$_2$SO$_4$), filtered and evaporated. The residue was purified by chromatography (SiO$_2$, CH$_2$Cl$_2$/ethyl acetate 19:1) to give 2.20 g (70%) [5-(2-chloro-phenyl)-2-methylsulfanyl-pyrimidin-4-yl]-carbamic acid tert.-butyl ester as a colorless solid, MS (EI): 351 (M$^+$).

b) [5-(2-Chloro-phenyl)-2-methylsulfanyl-pyrimidin-4-yl]-methyl-carbamic acid tert.-butyl ester To a solution of 2.0 g (5.68 mmol) [5-(2-chloro-phenyl)-2-methylsulfanyl-pyrimidin-4-yl]-carbamic acid tert.-butyl ester in 30 ml N,N-dimethylformamide 0.34 g (8.53 mmol) sodiumhydride (60% dispersion in mineraloil) was added and the reaction mixture stirred for 1 hr. After the addition of 0.56 ml (9.09 mmol) methyl iodide at 0°, the reaction mixture was stirred for 3 hrs. The reaction mixture was distributed between 75 ml H$_2$O, 75 ml brine and 75 ml CH$_2$Cl$_2$. The phases were separated, the aqueous layer washed twice with 75 ml CH$_2$Cl$_2$. The combined organic layers were dried (Na$_2$SO$_4$), filtered and evaporated. The residue was purified by chromatography (SiO$_2$, CH$_2$Cl$_2$/ethyl acetate 19:1) to give 2.0 g (96%) [5-(2-chloro-phenyl)-2-methylsulfanyl-pyrimidin-4-yl]-methyl-carbamic acid tert.-butyl ester as a pale yellow oil, MS (EI): 365 (M$^+$).

c) [5-(2-Chloro-phenyl)-2-methylsulfanyl-pyrimidin-4-yl]-methyl-amine

A solution of 2.40 g (6.5 mmol) [5-(2-chloro-phenyl)-2-methylsulfanyl-pyrimidin-4-yl]-methyl-carbamic acid tert-butyl ester in 30 ml MeOH/HCl (2N) was stirred at 55° for 3 hrs. After evaporation of the solvent, the residue was distributed between 40 ml 1N NaOH and 40 ml CH$_2$Cl$_2$. The phases were separated, the aqueous layer washed twice with 50 ml CH$_2$C$_2$. The combined organic layers were dried (Na$_2$SO$_4$), filtered and evaporated. The residue was purified by chromatography (SiO$_2$, CH$_2$Cl$_2$/ethyl acetate 19:1) to give 1.70 g (97%) [5-(2-chloro-phenyl)-2-methylsulfanyl-pyrimidin-4-yl]-methyl-amine as a white solid, MS (EI): 265 (M$^+$).

d) 2-(3,5-Bis-trifluoromethyl-phenyl)-N-[5-(2-chloro-phenyl)-2-methylsulfanyl-pyrimidin-4-yl]-N-methyl-isobutyramide To a solution of 0.70 g (2.6 mmol) [5-(2-Chloro-phenyl)-2-methylsulfanyl-pyrimidin-4-yl]-methyl-amine in 4 ml N,N-dimethylformamide 2.6 ml of a 1M solution potassiumhexamethyldisilazide (2.6 mmol) in THF were added at 0°. After 1 h, 0.92 g (2.6 mmol) (2-(3,5-bis-trifluoromethyl-phenyl)-2-methyl-propionyl chloride in 2 ml THF were added and the reaction mixture stirred for 24 hrs. at RT. The reaction mixture was poured onto 50 ml 0.5 N NaOH-solution. After addition of ethyl acetate the phases were separated, the aqueous layer washed twice with 50 ml ethyl acetate. The combined organic layers were dried (Na$_2$SO$_4$), filtered and evaporated. The residue was purified by chromatography (SiO$_2$, CH$_2$Cl$_2$/ethyl acetate 19:1) to give 0.85 g (58%) 2-(3,5-bis-trifluoromethyl-phenyl)-N-[5-(2-chloro-phenyl)-2-methylsulfanyl-pyrimidin-4-yl]-N-methyl-isobutyramide as a white foam, MS (EI): 547 (M$^+$).

EXAMPLE 81

2-(3,5-Bis-trifluoromethyl-phenyl)-N-[5-(2-chloro-phenyl)-2-methanesulfonyl-pyrimidin-4-yl]-N-methyl-isobutyramide To a solution of 0.8 g (1.64 mmol) 2-(3,5-bis-trifluoromethyl-phenyl)-N-[5-(2-chloro-phenyl)-2-methylsulfanyl-pyrimidin-4-yl]-N-methyl-isobutyramide in 50 ml CH$_2$Cl$_2$ 0.89 g (3.65 mmol) 3-chloroperbenzoic acid (70%) was added at 5° and the reaction mixture stirred for 3 hrs. at RT. After addition of 100 ml sat. NaHCO$_3$-solution, the layers were separated, the organic phase washed with sat. NaHCO$_3$-solution, dried (Na$_2$SO$_4$), filtered and evaporated. The residue was purified by chromatography (SiO$_2$, CH$_2$Cl$_2$/ethyl acetate) to give 0.73 g (86%) 2-(3,5-bis-trifluoromethyl-phenyl)-N-[5-(2-chloro-phenyl)-2-methanesulfonyl-pyrimidin-4-yl]-N-methyl-isobutyramide as a colorless foam, MS (ISP):580.0 (M+H$^+$).

EXAMPLE 82

2-(3,5-Bis-trifluoromethyl-phenyl)-N-[5-(2-chloro-phenyl)-2-(4-methyl-piperazin-1-yl)-pyrimidin-4-yl]-N-methyl-isobutyramide To a solution of 0.3 g (0.52 mmol) 2-(3,5-bis-trifluoromethyl-phenyl)-N-[5-(2-chloro-phenyl)-2-methanesulfonyl-pyrimidin-4-yl]-N-methyl-isobutyramide in 10 ml dioxane 0.14 ml (1.29 mmol) 1-methylpiperazine was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH₂Cl₂, the combined organic layers dried (MgSO₄), filtered and evaporated. The residue was purified by chromatography (SiO₂, CH₂Cl₂/MeOH/NH₄OH 140:10:1) to give 0.25 g (80%) 2-(3,5-bis-trifluoromethyl-phenyl)-N-[5-(2-chloro-phenyl)-2-(4-methyl-piperazin-1-yl)-pyrimidin-4-yl]-N-methyl-isobutyramide as a colorless foam, MS (ISP): 600.1 (M+H⁺).

EXAMPLE 83

2-(3,5-Bis-trifluoromethyl-phenyl)-N-[5-(2-chloro-phenyl)-2-(2-dimethylamino-ethylamino)-pyrimidin-4-yl]-N-methyl-isobutyramide To a solution of 0.4 g (0.69 mmol) 2-(3,5-bis-trifluoromethyl-phenyl)-N-[5-(2-chloro-phenyl)-2-methanesulfonyl-pyrimidin-4-yl]-N-methyl-isobutyramide in 10 ml dioxane 0.19 ml (1.72 mmol) 2-dimethylaminoethylamin was added. The reaction mixture was stirred for 16 hrs. After evaporation of the solvent, the residue was distributed between 50 ml CH₂Cl₂ and 50 ml H₂O. The aqueous layer was extracted with 50 ml CH₂Cl₂, the combined organic layers dried (MgSO₄), filtered and evaporated. The residue was purified by chromatography (SiO₂, CH₂Cl₂/MeOH/NH₄OH 110:10:1) to give 0.30 g (74%) 2-(3,5-bis-trifluoromethyl-phenyl)-N-[5-(2-chloro-phenyl)-2-(2-dimethylamino-ethylamino)-pyrimidin-4-yl]-N-methyl-isobutyramide as a colorless foam, MS (ISP): 588.2 (M+H⁺).

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

Example C

Suppositories of the following composition are manufactured:

|  | mg/supp |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:
1. A compound of the general formula

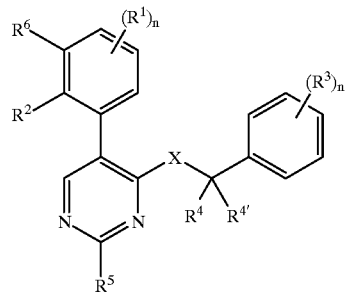

wherein
R¹ is hydrogen or halogen;
R² is hydrogen, halogen, lower alkyl or lower alkoxy;
R³ is halogen, trifluoromethyl, lower alkoxy or lower alkyl;
R⁴ and R⁴" are each independently hydrogen or lower alkyl;
R⁵ is lower alkyl, lower alkoxy, amino, hydroxy, hydroxy-lower alkyl, —(CH₂)ₙ-piperazinyl, piperazinyl substituted by lower alkyl, —(CH₂)ₙ-morpholinyl, —(CH₂)ₙ₊₁-imidazolyl, —O—(CH₂)ₙ₊₁-morpholinyl, —O—(CH₂)ₙ₊₁-piperidinyl, lower alkyl-sulfanyl, lower alkyl-sulfonyl, benzylamino, —NH—(CH₂)ₙ₊₁N(R⁴")₂, —(CH₂)ₙ—NH—(CH₂)ₙ₊₁N(R⁴")₂, —(CH₂)ₙ₊₁N(R⁴")₂, or —O—(CH₂)ₙ₊₁N(R⁴")₂, wherein R⁴" is hydrogen or lower alkyl;
R⁶ is hydrogen;
R² and R⁶ or R¹ and R⁶ may together be —CH=CH—CH=CH—, wherein R² and R⁶ or R¹ and R⁶, respectively, together with the two carbon ring atoms to which they are attached form a fused ring, with the proviso that n for R¹ is 1;
n is independently 0–2; and
X is —C(O)N(R⁴")— or —N(R⁴")C(O)—;
or pharmaceutically acceptable acid addition salts thereof.
2. The compound according to claim 1, wherein X is —C(O)N(R⁴")—, R⁴" is methyl and R⁵ is —(CH₂)ₙ-piperazinyl, or piperazinyl substituted by methyl and n is 0 or 1.

3. The compound according to claim 2, which is selected from the group consisting of:

5-(2-chloro-phenyl)-2-(4-methyl-piperazin-1-yl)-pyrimidine-4-carboxylic acid (3,5-bis-trifluoromethyl-benzyl)-methyl-amide,
5-(4-fluoro-2-methyl-phenyl)-2-(4-methyl-piperazin-1-yl)-pyrimidine-4-carboxylic acid (3,5-bis-trifluoromethyl-benzyl)-methyl-amide, and
5-(2-chloro-phenyl)-2-(4-methyl-piperazin-1-ylmethyl)-pyrimidine-4-carboxylic acid (3,5-bis-trifluoromethyl-benzyl)-methyl-amide.

4. The compound according to claim 1, in which X is —C(O)N($R^{4''}$)—, $R^{4''}$ is methyl and $R^5$ is —O$(CH_2)_2$-morpholinyl.

5. The compound according to claim 4, which is 5-(2-chloro-phenyl)-2-(2-morpholin-4-yl-ethoxy)-pyrimidine-4-carboxylic acid (3,5-bis-trifluoromethyl-benzyl)-methyl-amid.

6. The compound according to claim 1, in which X is —C(O)N($R^{4''}$)—, $R^{4''}$ is methyl and $R^5$ is —NH$(CH_2)_{n+1}$N$(CH_3)_2$, —$(CH_2)_n$—NH$(CH_2)_{n+1}$N$(CH_3)_2$ or —O$(CH_2)_{n+1}$N$(CH_3)_2$, wherein n is 1 or 2.

7. A compound according to claim 6, which is selected from the group consisting of:

5-(2-chloro-phenyl)-2-(2-dimethylamino-ethylamino)-pyrimidine-4-carboxylic acid (3,5-bis-trifluoromethyl-benzyl)-methyl-amide,
2-(2-dimethylamino-ethylamino)-5-o-tolyl-pyrimidine-4-carboxylic acid (3,5-bis-trifluoromethyl-benzyl)-methyl-amide,
2-(2-dimethylamino-ethylamino)-5-(2-methoxy-phenyl)-pyrimidine-4-carboxylic acid (3,5-bis-trifluoromethyl-benzyl)-methyl-amide,
2-(2-dimethylamino-ethylamino)-5-(4-fluoro-phenyl)-pyrimidine-4-carboxylic acid (3,5-bis-trifluoromethyl-benzyl)-methyl-amide,
2-(2-dimethylamino-ethylamino)-5-(4-fluoro-2-methyl-phenyl)-pyrimidine-4-carboxylic acid (3,5-bis-trifluoromethyl-benzyl)-methyl-amide,
5-(2-chloro-phenyl)-2-(3-dimethylamino-propoxy)-pyrimidine-4-carboxylic acid (3,5-bis-trifluoromethyl-benzyl)-methyl-amide,
5-(2-chloro-phenyl)-2-(2-dimethylamino-ethoxy)-pyrimidine-4-carboxylic acid (3,5-bis-trifluoromethyl-benzyl)-methyl-amide,
2-(2-dimethylamino-ethoxy)-5-o-tolyl-pyrimidine-4-carboxylic acid (3,5-bis-trifluoromethyl-benzyl)-methyl-amide,
2-(3-dimethylamino-propoxy)-5-o-tolyl-pyrimidine-4-carboxylic acid (3,5-bis-trifluoromethyl-benzyl)-methyl-amide,
2-(2-dimethylamino-propoxy)-5-(2-methoxy-phenyl)-pyrimidine-4-carboxylic acid (3,5-bis-trifluoromethyl-benzyl)-methyl-amide,
2-(3-dimethylamino-propoxy)-5-(4-fluoro-2-methyl-phenyl)-pyrimidine-4-carboxylic acid (3,5-bis-trifluoromethyl-benzyl)-methyl-amide,
2-(2-dimethylamino-ethoxy)-5-(4-fluoro-2-methyl-phenyl)-pyrimidine-4-carboxylic acid (3,5-bis-trifluoromethyl-benzyl)-methyl-amide, and
5-(2-chloro-phenyl)-2-[(2-dimethylamino-ethylamino)-methyl]-pyrimidine-4-carboxylic acid (3,5-bis-trifluoromethyl-benzyl)-methyl-amide.

8. The compound according to claim 1, wherein X is —CON($R^{4''}$)$_2$, $R^{4''}$ is methyl and $R^5$ is $SCH_3$.

9. The compound in accordance with claim 8, which is selected from the group consisting of:

2-methylsulfanyl-5-o-tolyl-pyrimidine-4-carboxylic acid (3,5-bis-trifluoromethyl-benzyl)-methyl-amide, and
5-(4-fluoro-2-methyl-phenyl)-2-methylsulfanyl-pyrimidine-4-carboxylic acid (3,5-bis-trifluoromethyl-benzyl)-methyl-amide.

10. The compound according to claim 1, wherein X is —CON($R^{4''}$)$_2$, $R^{4''}$ is methyl and $R^2$ and $R^6$ or $R^1$ and $R^6$ are together —CH=CH—CH=CH—, wherein $R^2$ and $R^6$ or $R^1$ and $R^6$, respectively, together with the two carbon ring atoms to which they are attached form a fused ring, with the proviso that n for $R^1$ is 1.

11. The compound in accordance with claim 10, which is selected from the group consisting of:

2-(4-methyl-piperazin-1-yl)-5-naphthalen-1-yl-pyrimidine-4-carboxylic acid (3,5-bis-trifluoromethyl-benzyl)-methyl-amide,
2-(2-dimethylamino-ethylamino)-5-naphthalen-1-yl-pyrimidine-4-carboxylic acid (3,5-bis-trifluoromethyl-benzyl)-methyl-amide,
2-(2-dimethylamino-ethoxy)-5-naphthalen-1-yl-pyrimidine-4-carboxylic acid (3,5-bis-trifluoromethyl-benzyl)-methyl-amide,
2-(2-morpholin-4-yl-ethoxy)-5-naphthalen-1-yl-pyrimidine-4-carboxylic acid (3,5-bis-trifluoromethyl-benzyl)-methyl-amide, and
2-(3-dimethylamino-propoxy)-5-naphthalen-1-yl-pyrimidine-4-carboxylic acid (3,5-bis-trifluoromethyl-benzyl)-methyl-amide.

12. The compound according to claim 1, wherein X is —N($R^{4''}$)C(O)—, $R^{4''}$ is lower alkyl and $R^5$ is —$(CH_2)_n$-piperazinyl, piperazinyl substituted by lower alkyl, —$(CH_2)_n$-morpholinyl, —NH—$(CH_2)_{n+1}$N$(CH_3)_2$ or —O—$(CH_2)_{n+1}$N$(CH_3)_2$.

13. The compound in accordance with claim 12, which is selected from the group consisting of:

2-(3,5-bis-trifluoromethyl-phenyl)-N-methyl-N-[2-(4-methyl-piperazin-1-yl)-5-o-tolyl-pyrimidin-4-yl]-isobutyramide,
2-(3,5-bis-trifluoromethyl-phenyl)-N-methyl-N-(2-piperazin-1-yl-5-o-tolyl-pyrimidin-4-yl)-isobutyramide,
2-(3,5-bis-trifluoromethyl-phenyl)-N-methyl-N-(2-morpholin-4-yl-5-o-tolyl-pyrimidin-4-yl)-isobutyramide,
2-(3,5-bis-trifluoromethyl-phenyl)-N-[2-(2-dimethylamino-ethylamino)-5-o-tolyl-pyrimidin-4-yl]-N-methyl-isobutyramide,
2-(3,5-bis-trifluoromethyl-phenyl)-N-[2-(2-dimethylamino-ethoxy)-5-o-tolyl-pyrimidin-4-yl]-N-methyl-isobutyramide,
2-(3,5-bis-trifluoromethyl-phenyl)-N-[5-(2-chloro-phenyl)-2-(4-methyl-piperazin-1-yl)-pyrimidin-4-yl]-N-methyl-isobutyramide, and
2-(3,5-bis-trifluoromethyl-phenyl)-N-[5-(2-chloro-phenyl)-2-(2-dimethylamino-ethylamino)-pyrimidin-4-yl]-N-methyl-isobutyramide.

14. A pharmaceutical composition comprising a compound according to claim 1 and at least one pharmaceutically acceptable excipient.

15. A method of treatment of a central nervous system disorder taken from the group consisting of anxiety, depression and psychosis in a patient in need of such treatment, comprising administering to the patient a compound in accordance with claim 1 in an effective amount between about 10 mg to about 1000 mg per day.

* * * * *